(12) United States Patent
Kim et al.

(10) Patent No.: US 10,306,773 B2
(45) Date of Patent: May 28, 2019

(54) MOUNTING STRUCTURE FOR MODULE IN ELECTRONIC DEVICE

(71) Applicant: Samsung Electronics Co., Ltd., Gyeonggi-do (KR)

(72) Inventors: Hyung Dal Kim, Gyeonggi-do (KR); Oh Hyuck Kwon, Gyeonggi-do (KR); Han Vit Kang, Gyeonggi-do (KR); Jun Young Kim, Gyeonggi-do (KR); Moon Kyeong Kim, Gyeonggi-do (KR); Sang Seob Kim, Gyeonggi-do (KR); Jung Sik Park, Gyeonggi-do (KR); Hee Seok Jung, Gyeonggi-do (KR); Sung Cho, Gyeonggi-do (KR); Heung Sik Shin, Gyeonggi-do (KR); Ji Woong Oh, Seoul (KR)

(73) Assignee: Samsung Electronics Co., Ltd (KR)

( * ) Notice: Subject to any disclaimer, the term of this patent is extended or adjusted under 35 U.S.C. 154(b) by 0 days.

(21) Appl. No.: 15/673,001

(22) Filed: Aug. 9, 2017

(65) Prior Publication Data
US 2018/0160545 A1 Jun. 7, 2018

(30) Foreign Application Priority Data

Dec. 5, 2016 (KR) .......................... 10-2016-0164694
Mar. 10, 2017 (KR) .......................... 10-2017-0030680

(51) Int. Cl.
*H05K 3/36* (2006.01)
*G06F 1/16* (2006.01)
(Continued)

(52) U.S. Cl.
CPC ............ *H05K 3/363* (2013.01); *A61B 5/1172* (2013.01); *G02F 1/1333* (2013.01);
(Continued)

(58) Field of Classification Search
USPC ......................................................... 361/749
See application file for complete search history.

(56) References Cited

U.S. PATENT DOCUMENTS 8,563,970 B2  10/2013  Choi et al.
9,117,401 B2   8/2015  Choi et al.
(Continued)

FOREIGN PATENT DOCUMENTS

KR    1020110051611    5/2011
KR    10-1190630       10/2012
(Continued)

OTHER PUBLICATIONS

European Search Report dated Mar. 27, 2018 issued in counterpart application No. 17190409.7-1221, 8 pages.
(Continued)

*Primary Examiner* — Andargie M Aychillhum
(74) *Attorney, Agent, or Firm* — The Farrell Law Firm, P.C.

(57) ABSTRACT

An electronic device is provided. The electronic device includes a display including a display area and a connecting area extending from one side of the display area, a flexible printed circuit board (FPCB) connected with the connecting area, and a first module mounted on a first surface of the FPCB, where the connecting area is bent such that the first module is apart from the display to face the display.

18 Claims, 17 Drawing Sheets

(51) Int. Cl.
　　　*G06K 9/00* (2006.01)
　　　*H05K 1/02* (2006.01)
　　　*G02F 1/1333* (2006.01)
　　　*H04M 1/02* (2006.01)
　　　*H05K 1/18* (2006.01)
　　　*H05K 3/34* (2006.01)
　　　*A61B 5/1172* (2016.01)
　　　*H05K 1/14* (2006.01)
　　　*G02F 1/1345* (2006.01)

(52) U.S. Cl.
　　　CPC ......... *G06F 1/1637* (2013.01); *G06K 9/0004* (2013.01); *G06K 9/00013* (2013.01); *H04M 1/0277* (2013.01); *H05K 1/028* (2013.01); *H05K 1/189* (2013.01); *H05K 3/3452* (2013.01); *G02F 1/13338* (2013.01); *G02F 1/13452* (2013.01); *H04M 2250/16* (2013.01); *H05K 1/147* (2013.01); *H05K 1/188* (2013.01); *H05K 2201/0154* (2013.01); *H05K 2201/056* (2013.01); *H05K 2201/099* (2013.01); *H05K 2201/10128* (2013.01); *H05K 2201/10628* (2013.01)

(56) References Cited

U.S. PATENT DOCUMENTS

| | | |
|---|---|---|
| 9,400,576 B2 | 7/2016 | Chen et al. |
| 9,456,062 B2 | 9/2016 | Oh |
| 9,462,097 B2 | 10/2016 | Oh |
| 9,769,919 B2 | 9/2017 | Park et al. |
| 9,880,690 B2 | 1/2018 | Oh |
| 9,939,978 B2 | 4/2018 | Chen et al. |
| 2008/0166028 A1 | 7/2008 | Turek et al. |
| 2009/0122026 A1 | 5/2009 | Oh |
| 2012/0162110 A1* | 6/2012 | Kobayashi ............ G06F 1/1643 345/173 |
| 2013/0021289 A1 | 1/2013 | Chen et al. |
| 2013/0089954 A1 | 4/2013 | Ro et al. |
| 2013/0193415 A1 | 8/2013 | Choi et al. |
| 2013/0320851 A1 | 12/2013 | Choi et al. |
| 2013/0323499 A1 | 12/2013 | Choi et al. |
| 2015/0036300 A1* | 2/2015 | Park ...................... H05K 1/147 361/749 |
| 2015/0192777 A1 | 7/2015 | Bae et al. |
| 2015/0296607 A1 | 10/2015 | Yang et al. |
| 2015/0306468 A1 | 10/2015 | Ueda et al. |
| 2015/0335295 A1 | 11/2015 | Park et al. |
| 2016/0212251 A1 | 7/2016 | Oh |
| 2016/0378228 A1 | 12/2016 | Oh |
| 2017/0359890 A1 | 12/2017 | Park et al. |
| 2017/0367173 A1 | 12/2017 | Park et al. |

FOREIGN PATENT DOCUMENTS

| | | |
|---|---|---|
| KR | 1020130087987 | 8/2013 |
| KR | 1020140064156 | 5/2014 |
| KR | 1020150134552 | 12/2015 |

OTHER PUBLICATIONS

International Search Report dated Nov. 3, 2017 issued in counterpart application No. PCT/KR2017/008125, 10 pages.
Korean Office Action dated Aug. 9, 2017 issued in counterpart application No. 10-2017-0030680, 18 pages.
Korean Office Action dated Dec. 19, 2017 issued in counterpart application No. 10-2017-0030680, 6 pages.

* cited by examiner

MOUNTING STRUCTURE FOR MODULE IN ELECTRONIC DEVICE

PRIORITY

This application claims priority under 35 U.S.C. § 119(a) to a Korean Patent Application filed on Dec. 5, 2016, in the Korean Intellectual Property Office and assigned Serial number 10-2016-0164694, and to a Korean Patent Application filed on Mar. 10, 2017, in the Korean Intellectual Property Office and assigned Serial number 10-2017-0030680, the entire disclosure of each of which is incorporated herein by reference.

BACKGROUND

1. Field of the Disclosure

The present disclosure relates generally to mounting structures for hardware modules included in electronic devices.

2. Description of the Related Art

Portable electronic devices, which are equipped with a display, such as smartphones, wearable devices, and the like are widely supplied since the spread of personal computers. The display of the portable electronic device may be implemented with a touch screen display including a touch panel. The touch screen display may function as an input device that is able to receive a user manipulation, in addition to a visual display device.

The size of the touch screen display mounted in the portable electronic device (e.g., a smartphone) tends to range from 3 inches to 5 inches or larger to satisfy user demand. According to a trend to enlarge the touch screen display, the touch screen display may occupy most parts of a front surface of the electronic device.

SUMMARY

The present disclosure has been made to address at least the above-mentioned problems and/or disadvantages and to provide at least the advantages described below.

Accordingly, an aspect of the present disclosure is to provide mounting structures in an electronic device for hardware modules (e.g., pressure sensors, biometric sensors, and the like) disposed below a touch screen display of the electronic device, when the touch screen display constitutes substantially the entire front appearance of the electronic device, and an electronic device including the same.

Accordingly, another aspect of the present disclosure is to provide the functions of hardware modules of an electronic device which are mounted below a display that is disposed on substantially the entire area of a front surface of the electronic device, without negatively affecting the display and touch input functions of the display.

In accordance with an aspect of the present disclosure, an electronic device is provided. The electronic device includes a display including a display area and a connecting area extending from one side of the display area, a flexible printed circuit board (FPCB) connected with the connecting area, and a first module mounted on a first surface of the FPCB, where the connecting area is bent such that the first module is apart from the display to face the display.

In accordance with another aspect of the present disclosure, an electronic device is provided. The electronic device includes a flexible printed circuit board (FPCB) including a planar area and a bent area, a sensor mounted on a first surface of the planar area, and a display connected with the bent area, where the bent area is bent such that the sensor is apart from the display to face the display.

In accordance with another aspect of the present disclosure, a display device is provided. The display device includes a display panel having a plurality of pixels to display content, a flexible member including a first area making contact with one surface of the display panel and a second area extending from the one surface of the display panel, a display driver integrated circuit disposed in the second area of the flexible member, a flexible printed circuit board (FPCB) connected with the second area, and a biometric sensor mounted on one surface of the FPCB.

BRIEF DESCRIPTION OF THE DRAWINGS

The above and other aspects, features, and advantages of the present disclosure will be more apparent from the following description taken in conjunction with the accompanying drawings, in which.

DETAILED DESCRIPTION OF EMBODIMENTS OF THE PRESENT DISCLOSURE

Figure 1:
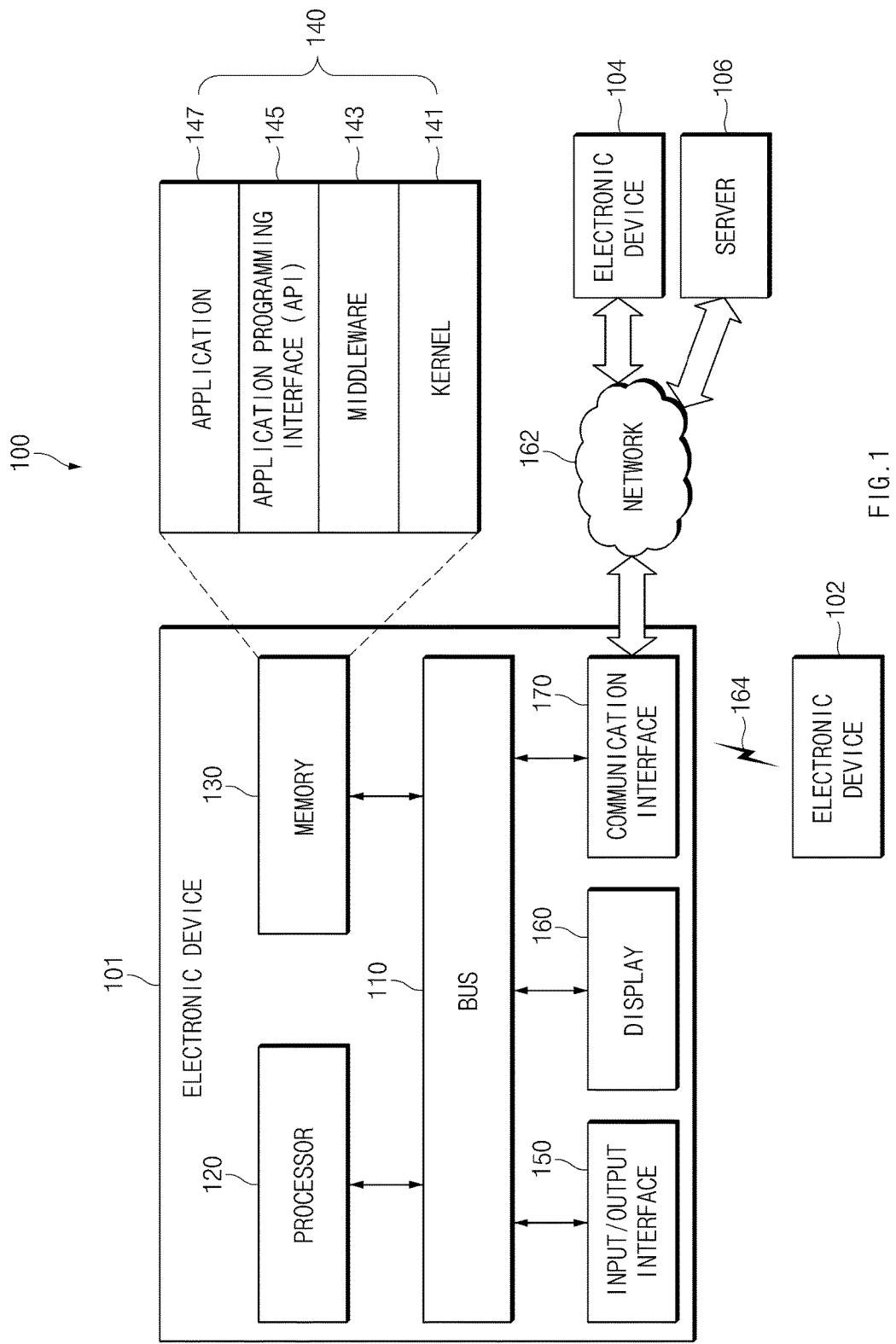
FIG. 1 is a block diagram of a network environment including an electronic device, according to an embodiment of the present disclosure.

Hereinafter, various embodiments of this disclosure will be described with reference to accompanying drawings, in which similar elements may be marked by similar reference numerals. However, this description provided herein is not intended to limit the present disclosure to the described embodiments and those skilled in the art will recognize that modifications, equivalents, and/or alternatives of the various embodiments described herein can be made without departing from the scope and spirit of this disclosure. In this disclosure, the expressions "have", "include" and "comprise", indicate the existence of corresponding features (e.g., elements such as numeric values, functions, operations, or components) but do not exclude the presence of additional features.

In this disclosure, the expressions "A or B", "at least one of A or/and B", or "one or more of A or/and B", may include any and all combinations of one or more of the associated listed items. For example, the term "A or B", "at least one of A and B", or "at least one of A or B" may refer to the case (1) where A is included, the case (2) where B is included, or the case (3) where both A and B are included.

In this disclosure, terms such as "first", "second", and the like are used to refer to various elements regardless of the order and/or the priority and to distinguish the relevant elements from other elements, but do not limit the elements. For example, "a first user device" and "a second user device" indicate different user devices regardless of the order or the priority. For example, a first element may be referred to as a second element, and similarly, a second element may be referred to as a first element.

It will be understood that when an element (e.g., a first element) is referred to as being "coupled" or "connected" with/to another element (e.g., a second element), the element may be directly coupled or connected with/to the other element or an intervening element (e.g., a third element) may be present. In contrast, when an element (e.g., a first element) is referred to as being "directly coupled" or "directly connected" with/to another element (e.g., a second element), it should be understood that there is no intervening element (e.g., a third element).

According to the situation, the expression "configured to" used in this disclosure may be used interchangeably with the expressions "suitable for", "having the capacity to", "designed to", "adapted to", "made to", or "capable of". The term "configured to" does not mean only "specifically designed to" in hardware. Instead, the expression "a device configured to" may mean that the device is "capable of" operating together with another device or other components. For example, a "processor configured to (or set to) perform A, B, and C" may mean a dedicated processor (e.g., an embedded processor) for performing a corresponding operation or a generic-purpose processor (e.g., a central processing unit (CPU) or an application processor (AP)) which performs corresponding operations by executing one or more software programs which are stored in a memory device.

Terms used in this disclosure are used to describe specified embodiments and are not intended to limit the scope of another embodiment. The terms of a singular form may include plural forms unless otherwise specified. Unless otherwise indicated herein, all the terms used herein, which include technical or scientific terms, may have the same meanings that are generally understood by those skilled in the art to which this disclosure pertains. It should be understood that terms that are defined in a general dictionary and are commonly used should be interpreted as having meanings equivalent to those which are customary in the relevant art, and should not be interpreted in an idealized or overly formal manner, unless expressly so defined in this disclosure. In some cases, even if certain terms are defined in this disclosure, they may not be interpreted to exclude embodiments of this disclosure.

An electronic device according to various embodiments of the present disclosure may include at least one of smartphones, tablet personal computers (PCs), mobile phones, video telephones, electronic book readers, desktop PCs, laptop PCs, netbook computers, workstations, servers, personal digital assistants (PDAs), portable multimedia players (PMPs), motion picture experts group (MPEG-1 or MPEG-2) audio layer 3 (MP3) players, mobile medical devices, cameras, or wearable devices. The wearable device may include at least one of an accessory type (e.g., watches, rings, bracelets, anklets, necklaces, glasses, contact lens, or head-mounted-devices (HMDs), a fabric or garment-integrated type (e.g., an electronic apparel), a body-attached type (e.g., a skin pad or tattoos), or a bio-implantable type (e.g., an implantable circuit).

The electronic device may be a home appliance. The home appliances may include at least one of televisions (TVs), digital versatile disc (DVD) players, audio devices, refrigerators, air conditioners, cleaners, ovens, microwave ovens, washing machines, air cleaners, set-top boxes, home automation control panels, security control panels, TV boxes (e.g., Samsung HomeSync™, Apple TV™, and Google TV™), game consoles (e.g., Xbox™ and PlayStation™), electronic dictionaries, electronic keys, camcorders, electronic picture frames, and the like.

The electronic device may include at least one of various medical devices (e.g., various portable medical measurement devices (e.g., blood glucose monitoring devices, heartbeat measuring devices, blood pressure measuring devices, body temperature measuring devices, and the like), magnetic resonance angiography (MRA) devices, magnetic resonance imaging (MRI) devices, computed tomography (CT) devices, scanners, and ultrasonic devices), navigation devices, global navigation satellite systems (GNSS), event data recorders (EDRs), flight data recorders (FDRs), vehicle infotainment devices, electronic equipment for vessels (e.g., navigation systems and gyrocompasses), avionics, security devices, head units for vehicles, industrial or home robots, automatic teller machines (ATMs), point of sales (POSs) devices, or Internet of things (IoT) devices (e.g., light bulbs, various sensors, electric or gas meters, sprinkler devices, fire alarms, thermostats, street lamps, toasters, exercise equipment, hot water tanks, heaters, boilers, and the like).

The electronic device may include at least one of parts of furniture or buildings/structures, electronic boards, electronic signature receiving devices, projectors, or various measuring instruments (e.g., water meters, electricity meters, gas meters, or wave meters, and the like).

The electronic device may be a flexible electronic device.

The electronic device may be one of the above-described devices or a combination thereof. Furthermore, the electronic device may not be limited to the above-described electronic devices and may include other electronic devices and new electronic devices according to future technology developments.

In this disclosure, the term "user" may refer to a person who uses an electronic device or may refer to a device (e.g., an artificial intelligence electronic device) that uses the electronic device.

FIG. 1 is a block diagram of a network environment including an electronic device, according to an embodiment of the present disclosure.

Referring to FIG. 1, a network environment 100 including an electronic device 101 is provided. The electronic device 101 includes a bus 110, a processor 120, a memory 130, an input/output interface 150, a display 160, and a communication interface 170. The electronic device 101 may omit at least one of the above-described elements or may further include other element(s).

The bus 110 interconnects the above-described elements 110 to 170 and may include a circuit for conveying communications (e.g., a control message and/or data) among the above-described elements.

The processor 120 may include one or more of a CPU, an AP, or a communication processor (CP). The processor 120 may perform an arithmetic operation or data processing associated with control and/or communication of at least one other element of the electronic device 101.

The memory 130 may include a volatile and/or nonvolatile memory. The memory 130 may store instructions or data associated with at least one other element of the electronic device 101. The memory 130 may store software and/or a program 140. The program 140 may include a kernel 141, a middleware 143, an application programming interface (API) 145, and/or at least one application 147. At least a part of the kernel 141, the middleware 143, or the API 145 may be referred to as an operating system (OS).

The kernel 141 controls or manages system resources (e.g., the bus 110, the processor 120, the memory 130, etc.) that are used to execute operations or functions of other programs (e.g., the middleware 143, the API 145, and the application 147). Furthermore, the kernel 141 may provide an interface that allows the middleware 143, the API 145, or the application 147 to access discrete elements of the electronic device 101 so as to control or manage system resources.

The middleware 143 may serve as an intermediary such that the API 145 or the application 147 communicates with the kernel 141 to exchange data.

Furthermore, the middleware 143 may process one or more task requests received from the application 147 according to a priority order. For example, the middleware 143 may assign a priority for using the system resources (e.g., the bus 110, the processor 120, the memory 130, etc.) of the electronic device 101 to at least one application 147. The middleware 143 may process the one or more task requests according to the priority assigned to the at least one application 147, thereby performing scheduling or load balancing on the one or more task requests.

The API 145 is an interface through which the application 147 controls a function provided by the kernel 141 or the middleware 143, and may include at least one interface or function (e.g., an instruction) for file control, window control, image processing, character control, or the like.

The input/output interface 150 may serve as an interface which transmits an instruction or data input from a user or an external device to other elements of the electronic device 101. Furthermore, the input/output interface 150 may output an instruction or data, received from other elements of the electronic device 101, to a user or an external device.

The display 160 may include a liquid crystal display (LCD), a light-emitting diode (LED) display, an organic LED (OLED) display, a microelectromechanical systems (MEMS) display, or an electronic paper display. The display 160 may display various contents (e.g., a text, an image, a video, an icon, a symbol, and the like) to a user. The display 160 may include a touch screen and may receive a touch, gesture, proximity, or hovering input using an electronic pen or a part of a user's body.

The communication interface 170 may establish communication between the electronic device 101 and a first external electronic device 102, a second external electronic device 104, or a server 106. The communication interface 170 may be connected to the first external electronic device 102 through short-range communication 164 and may be connected to the second external electronic device 104 and the server 106 through a network 162 over wireless communication or wired communication to communicate with the external device.

The wireless communication may include cellular communication employing at least one of long-term evolution (LTE), LTE Advanced (LTE-A), code division multiple access (CDMA), wideband CDMA (WCDMA), universal mobile telecommunications system (UMTS), wireless broadband (WiBro), global system for mobile communications (GSM), or the like, as cellular communication protocol. The wireless communication may include the short-range communication 164. The short-range communication 164 may include at least one of Wi-Fi, Bluetooth (BT), Bluetooth low energy (BLE), Zigbee, near field communication (NFC), magnetic stripe transmission (MST), radio frequency (RF), a body area network (BAN), and GNSS.

The MST may generate a pulse in response to transmission of data using an electromagnetic signal, and the pulse may generate a magnetic field signal. The electronic device 101 may transfer the magnetic field signal to a POS device, and the POS device may detect the magnetic field signal using an MST reader. The POS device may recover the data by converting the detected magnetic field signal to an electrical signal.

The GNSS may include at least one of a global positioning system (GPS), a global navigation satellite system (Glonass), a Beidou navigation satellite system (Beidou), or Galileo, a European global satellite-based navigation system based on an available region, a bandwidth, or the like. Hereinafter, the terms "GPS" and "GNSS" may be interchangeably used.

The wired communication may include at least one of a universal serial bus (USB), a high definition multimedia interface (HDMI), a recommended standard-232 (RS-232), a plain old telephone service (POTS), or the like.

The network 162 may include at least one of telecommunications networks a computer network (e.g., local area network (LAN) or a wide area network (WAN)), the Internet, or a telephone network.

Each of the first and second external electronic devices 102 and 104 may be a device of which the type is different from or the same as that of the electronic device 101. The server 106 may include a group of one or more servers. All or a part of operations performed in the electronic device 101 may be executed by one or more external electronic devices (e.g., the first and second external electronic devices 102 and 104 or the server 106). In the case where the electronic device 101 executes any function or service automatically or in response to a request, the electronic device 101 may not perform the function or the service internally, but alternatively or additionally, may request at least a part of the function from another device (e.g., the first or second external electronic device 102 or 104 or the server 106). The other electronic device may execute the requested function or additional function and may transmit the execution result to the electronic device 101. The electronic device 101 may provide the requested function or service using the received result or may additionally process the received result to provide the requested function or service. To this end cloud computing, distributed computing, or client-server computing may be used.

Figure 2:
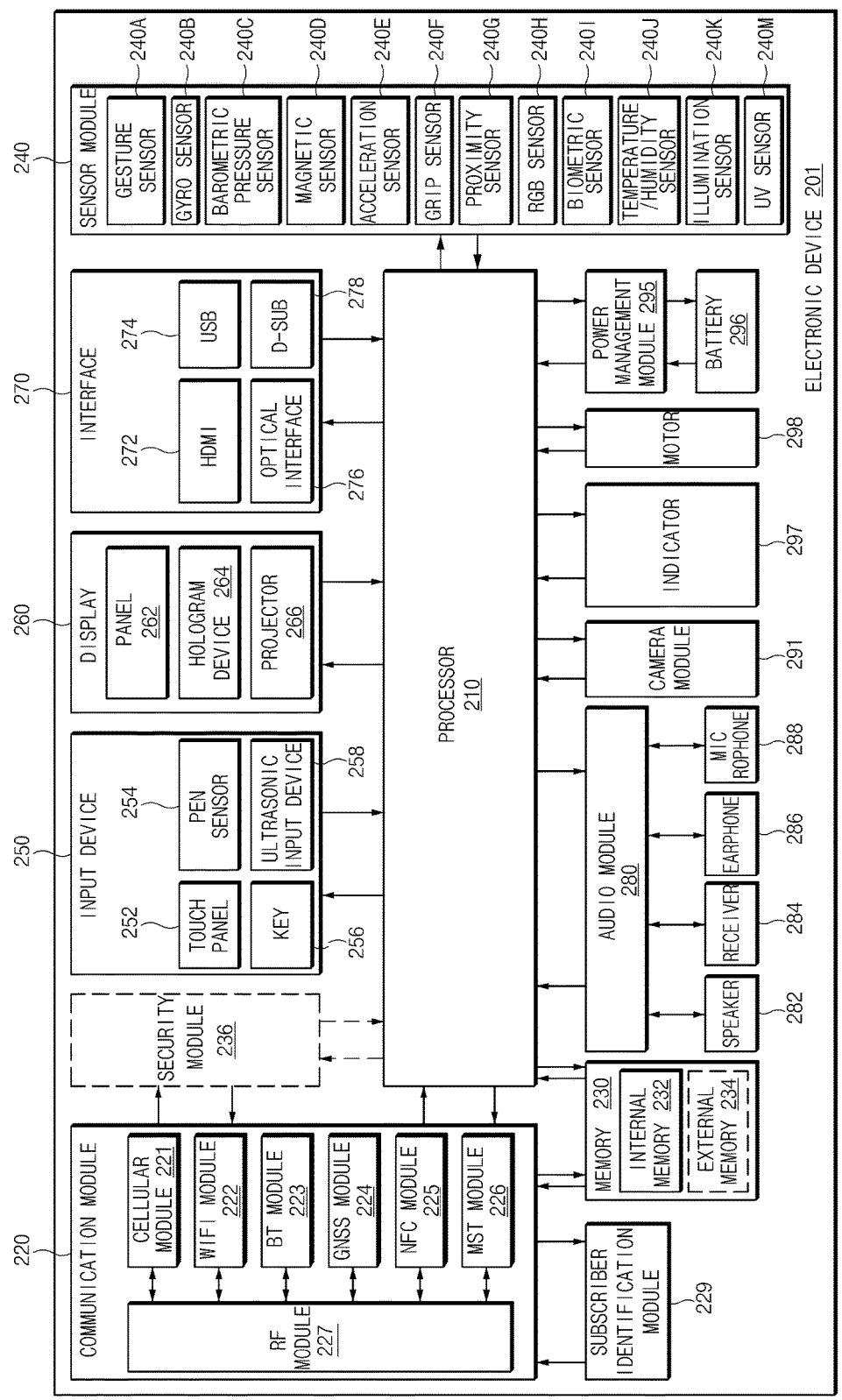
FIG. 2 is a block diagram of a configuration of an electronic device, according to an embodiment of the present disclosure.

FIG. 2 is a block diagram of a configuration of an electronic device, according to an embodiment of the present disclosure.

Referring to FIG. 2, an electronic device 201 is provided. The electronic device 201 includes at least one processor 210, a communication module 220, a subscriber identification module (SIM) 229, a memory 230, a security module 236, a sensor module 240, an input device 250, a display 260, an interface 270, an audio module 280, a camera module 291, a power management module 295, a battery 296, an indicator 297, and a motor 298.

The processor 210 may operate an OS or an application to control a plurality of hardware or software elements connected to the processor 210 and may process and compute a variety of data. The processor 210 may be implemented with a system on chip (SoC). The processor 210 may further include a graphic processing unit (GPU) and/or an image signal processor (ISP). The processor 210 may include at least a part (e.g., a cellular module 221) of the elements of the electronic device 201. The processor 210 may load an instruction or data, which is received from at least one of the other elements (e.g., a nonvolatile memory), into a volatile memory and process the loaded instruction or data. The processor 210 may store a variety of data in the nonvolatile memory.

The communication module 220 may include the cellular module 221, a Wi-Fi module 222, a BT module 223, a GNSS module 224 (e.g., a GPS module, a Glonass module, a Beidou module, or a Galileo module), an NFC module 225, an MST module 226, and an RF module 227.

The cellular module 221 may provide voice communication, video communication, a text message service, an Internet service, or the like over a communication network. The cellular module 221 may perform identification and authentication of the electronic device 201 within a communication network by using the SIM 229. The cellular module 221 may perform at least a part of functions that the processor 210 provides. The cellular module 221 may include a CP.

Each of the Wi-Fi module 222, the BT module 223, the GNSS module 224, the NFC module 225, and the MST module 226 may include a processor for processing data exchanged through the module. At least a part of the communication module 220, such as the cellular module 221, the Wi-Fi module 222, the BT module 223, the GNSS module 224, the NFC module 225, or the MST module 226, may be included within one integrated circuit (IC) or an IC package.

The RF module 227 may transmit and receive a communication signal (e.g., an RF signal). The RF module 227 may include a transceiver, a power amplifier module (PAM), a frequency filter, a low noise amplifier (LNA), an antenna, or the like. Alternatively or additionally, at least one of the cellular module 221, the Wi-Fi module 222, the BT module 223, the GNSS module 224, the NFC module 225, or the MST module 226 may transmit and receive an RF signal through a separate RF module.

The SIM 229 may include a card containing the SIM and/or embedded SIM and may include unique identification information (e.g., an integrated circuit card identifier (ICCID)) or subscriber information (e.g., international mobile subscriber identity (IMSI)).

The memory 230 may include an internal memory 232 and/or an external memory 234.

The internal memory 232 may include at least one of a volatile memory (e.g., a dynamic random access memory (DRAM), a static RAM (SRAM), a synchronous DRAM (SDRAM), or the like), a nonvolatile memory (e.g., a one-time programmable read only memory (OTPROM), a programmable ROM (PROM), an erasable and programmable ROM (EPROM), an electrically erasable and programmable ROM (EEPROM), a mask ROM, a flash ROM, a flash memory (e.g., a NAND flash memory or a NOR flash memory), or the like), a hard drive, or a solid state drive (SSD).

The external memory 234 may include a flash drive such as compact flash (CF), secure digital (SD), micro secure digital (Micro-SD), mini secure digital (Mini-SD), extreme digital (xD), a multimedia card (MMC), a memory stick, or the like. The external memory 234 may be operatively and/or physically connected to the electronic device 201 through various interfaces.

A security module 236 is a module that includes a storage space of which a security level is higher than that of the memory 230 and may be a circuit that guarantees safe data storage and a protected execution environment. The security module 236 may be implemented with a separate circuit and may include a separate processor. The security module 236 may be in a smart chip or an SD card, which is removable, or may include an embedded secure element (eSE) embedded in a fixed chip of the electronic device 201. Furthermore, the security module 236 may operate based on an OS that is different from the OS of the electronic device 201. For example, the security module 236 may operate based on java card open platform (JCOP) OS.

The sensor module 240 may measure a physical quantity or may detect an operational state of the electronic device 201. The sensor module 240 may convert the measured or detected information to an electrical signal. The sensor module 240 may include at least one of a gesture sensor 240A, a gyro sensor 240B, a barometric pressure sensor 240C, a magnetic sensor 240D, an acceleration sensor 240E, a grip sensor 240F, a proximity sensor 240G, a red, green, blue (RGB) sensor 240H, a biometric sensor 2401, a temperature/humidity sensor 240J, an illumination sensor 240K, or an ultraviolet (UV) sensor 240M. Additionally or alternatively, the sensor module 240 may further include an E-nose sensor, an electromyography (EMG) sensor, an electroencephalogram (EEG) sensor, an electrocardiogram (ECG) sensor, an infrared (IR) sensor, an iris sensor, and/or a fingerprint sensor. The sensor module 240 may further include a control circuit for controlling at least one or more of the sensors included therein. The electronic device 201 may further include a processor that is a part of the processor 210 or independent of the processor 210 and is configured to control the sensor module 240. The processor may control the sensor module 240 while the processor 210 remains at a sleep state.

The input device 250 includes a touch panel 252, a (digital) pen sensor 254, a key 256, and/or an ultrasonic input unit 258. The touch panel 252 may use at least one of capacitive, resistive, infrared, and ultrasonic detecting methods. Also, the touch panel 252 may further include a control circuit. The touch panel 252 may further include a tactile layer to provide a tactile reaction to a user.

The (digital) pen sensor 254 may be a part of a touch panel or may include an additional sheet for recognition.

The key 256 may include a physical button, an optical key, or a keypad.

The ultrasonic input device 258 may detect (or sense) an ultrasonic signal, which is generated from an input device, through a microphone 288 and may identify data corresponding to the detected ultrasonic signal.

The display 260 may include a panel 262, a hologram device 264, and/or a projector 266.

The panel 262 may be implemented to be flexible, transparent, and/or wearable. The panel 262 and the touch panel 252 may be integrated into a single module. The panel 262 may include a pressure sensor (or force sensor) that measures the intensity of touch pressure by a user. The pressure sensor may be implemented integrally with the touch panel 252, or may be implemented as at least one sensor, separately from the touch panel 252.

The hologram device 264 may display a stereoscopic image in the air using an interference of light.

The projector 266 may project light onto a screen to display an image. The screen may be arranged on the inside or the outside of the electronic device 201.

The display 260 may further include a control circuit for controlling the panel 262, the hologram device 264, or the projector 266.

The interface 270 may include a high-definition multimedia interface (HDMI) 272, a universal serial bus (USB) 274, an optical interface 276, or a D-subminiature (D-sub) 278. Additionally or generally, the interface 270 may include a mobile high definition link (MHL) interface, an SD card/MMC interface, or an infrared data association (IrDA) standard interface.

The audio module 280 may convert a sound into an electrical signal and vice versa. The audio module 280 may process sound information that is input or output through a speaker 282, a receiver 284, an earphone 286, or the microphone 288.

The camera module 291 may capture a still image or a video. The camera module 291 may include at least one or more image sensors (e.g., a front sensor or a rear sensor), a lens, an ISP, or a flash (e.g., an LED or a xenon lamp).

The power management module 295 may manage power of the electronic device 201. A power management integrated circuit (PMIC), a charger IC, or a battery gauge may be included in the power management module 295. The PMIC may use a wired charging method and/or a wireless charging method. The wireless charging method may include a magnetic resonance method, a magnetic induction method, or an electromagnetic method and may further include an additional circuit, for example, a coil loop, a resonant circuit, a rectifier, or the like. The battery gauge may measure a remaining capacity, a voltage, current, or temperature of the battery 296.

The battery 296 may include a rechargeable battery and/or a solar battery.

The indicator 297 may display a specific state of the electronic device 201 or a part of the electronic device 201(e.g., the processor 210), such as a booting state, a message state, a charging state, and the like.

The motor 298 may convert an electrical signal into a mechanical vibration and may generate a vibration or haptic effect, and the like.

A processing device (e.g., a GPU) for supporting a mobile TV may be included in the electronic device 201. The processing device for supporting the mobile TV may process media data according to the standards of digital multimedia broadcasting (DMB), digital video broadcasting (DVB), MediaFlo™, or the like.

Each of the above-mentioned elements of the electronic device 201 may be configured with one or more components, and the names of the elements may be changed according to the type of the electronic device. The electronic device 201 may include at least one of the above-mentioned elements, and some elements may be omitted or other additional elements may be added. Furthermore, some of the elements of the electronic device 201 may be combined with each other so as to form one entity, so that the functions of the elements may be performed in the same manner as before the combination.

Figure 3:
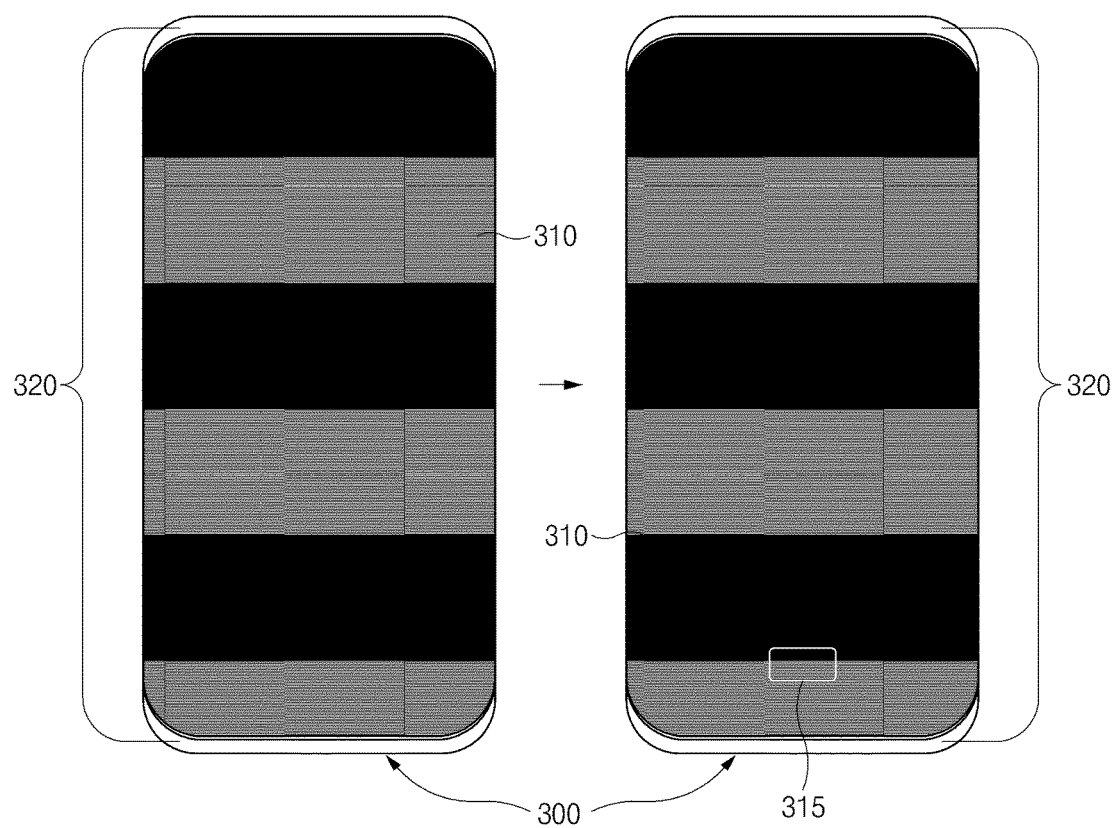
FIG. 3 illustrates a front view of an electronic device, according to an embodiment of the present disclosure.

FIG. 3 illustrates a front view of an electronic device, according to an embodiment of the present disclosure.

Referring to FIG. 3, an electronic device 300 is provided. The electronic device 300 includes a display 310 and a housing 320. The display 310 may occupy most parts of a front surface of the electronic device 300. A part of the housing 320, which forms a side surface of the electronic device 300 may be exposed through the front surface of the electronic device 300.

The electronic device 300 may display a guide image 315, which represents a home button, on the display 310, in response to a specified event (e.g., a touch, press against a physical button, motion detection by a gyro sensor/acceleration sensor, or the like) or in an always-on manner Hardware modules (e.g., a biometric sensor, a pressure sensor, and the like) may be disposed at an inner part of the electronic device 300 corresponding to the guide image 315.

Figure 4:
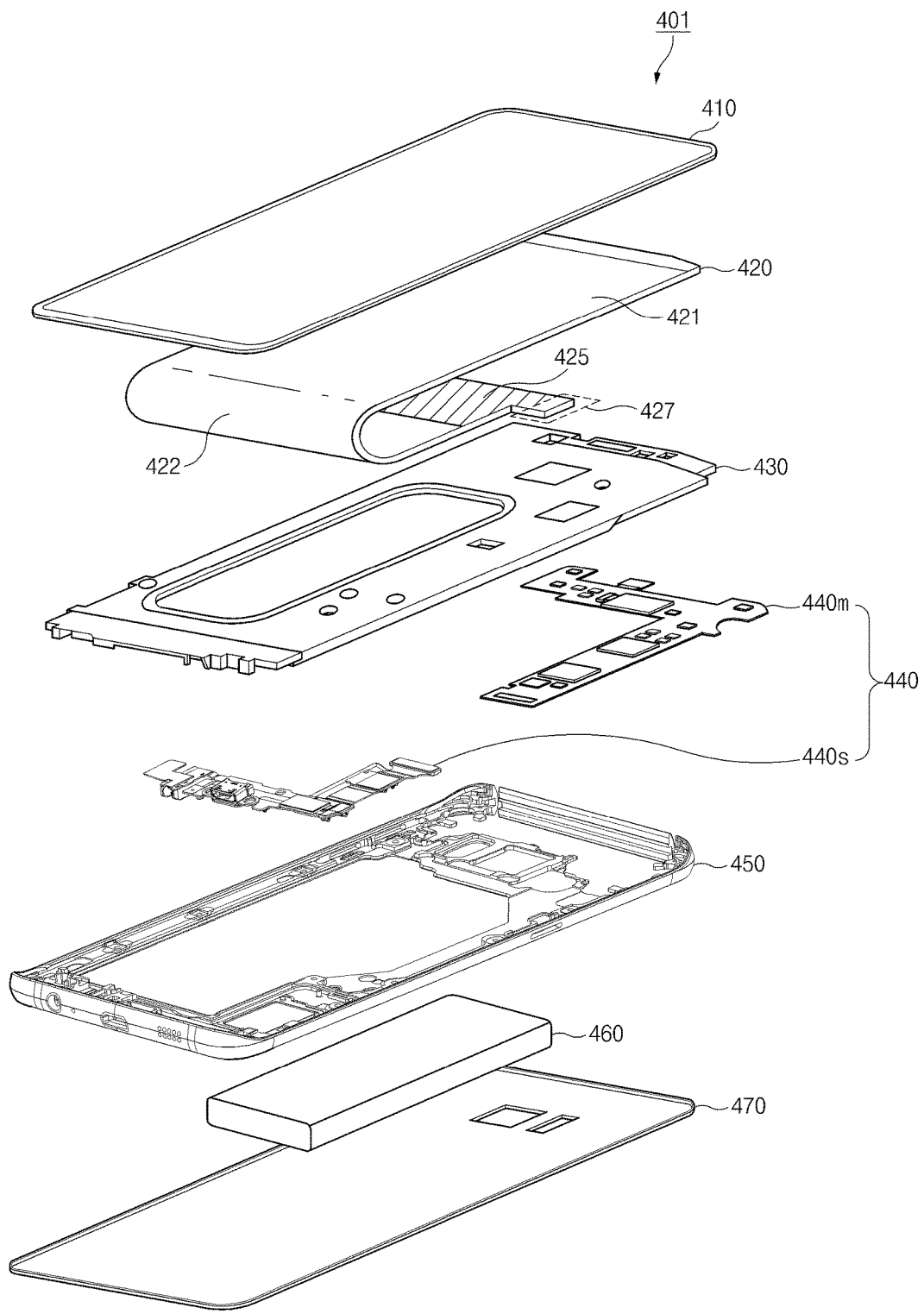
FIG. 4 illustrates an exploded perspective view of an electronic device, according to an embodiment of the present disclosure.

FIG. 4 illustrates an exploded perspective view of an electronic device, according to an embodiment of the present disclosure.

Referring to FIG. 4, an electronic device 401 is provided. The electronic device 401 may include a cover glass 410, a display device 420, a bracket 430, a circuit board 440, a rear housing 450, a battery 460, and/or a back cover 470. The electronic device 401 may omit one or more of the elements illustrated in FIG. 4, and may additionally include one or more elements which are not illustrated in FIG. 4.

The cover glass 410 may transmit light generated by the display device 420 when the light passes through the cover glass 410. In addition, a user may make a touch contact with a top of the cover glass 410 through an electronic pen or a part of the user's body (e.g., a finger). The cover glass 410 may be formed of, for example, tempered glass, reinforced plastic, a flexible polymer material, or the like and may protect the display device 420 or each element included in the electronic device 401 from an external impact. The cover glass 410 may be also referred to as a "glass window".

The display device 420 may be disposed below the cover glass 410 or may be coupled to the cover glass 410. Accordingly, the display device 420 may be exposed through at least a part of the cover glass 410. The display device 420 may output content (e.g., a text, an image, a video, an icon, a widget, a symbol, or the like) or may receive a touch input (including a touch, a gesture, and a hovering) from a user.

The display device 420 may include a display area 421 and a connecting area 422 extended from one side (lower side) of the display area 421. Pixels (e.g., OLEDs) may be disposed in the display area 421. The connecting area 422 may be electrically connected with an FPCB 425 disposed on a rear surface of the display device 420 through various conductive patterns (i.e., wirings). A side where the connecting area 422 starts to be extended, is not limited to the lower side of the display area 421. The connecting area 422 may, alternatively, be extended from an upper side, a left side, and a right side of the display area 421.

A part of the connecting area 422 may be folded toward the rear surface of the display area 421 such that the rear surface of the FPCB 425 is apart from the rear surface of the display area 421 to face the display area 421. The conductive pattern, which is formed in a partial area 427 of the FPCB 425, may pass a side surface of the bracket 430 and may be electrically connected with a main circuit board 440m of the circuit board 440 through a specified connector. Similarly to the display area 421, pixels may be arranged in the connecting area 422 depending on the design of the electronic device 401.

The display device 420 may include an LCD panel, an LED display panel, an OLED display panel, an MEMS display panel, or an electronic paper display panel. The display device 420 may include a capacitive touch panel, a pressure sensitive touch panel, a resistive touch panel, an infrared touch panel, or an ultrasonic touch panel. The touch panel may be inserted into a display panel (e.g., an add-on touch panel), may be directly formed on the display panel (e.g., an on-cell touch panel), or may be included in the display panel (e.g., an in-cell touch panel).

The bracket 430, which may be formed of a magnesium (Mg) alloy, may be disposed below the display device 420 and above the circuit board 440. The bracket 430 may be coupled to the display device 420 and the circuit board 440 to physically support the display device 420 and the circuit board 440. A swelling gap may be formed in the bracket 430 in consideration of swelling of the battery 460 which may occur due to deterioration of the battery 460.

The circuit board 440 may include the main circuit board 440m or a sub-circuit board 440s. The main circuit board 440m and the sub-circuit board 440s may be disposed below the bracket 430 and may be electrically connected with each other through a specified connector or a specified wiring. The main circuit board 440m and the sub-circuit board 440s may be implemented with rigid printed circuit boards (PCBs). Various electronic elements, devices, PCBs, or the like (e.g., a processor, a memory, a communication circuit, or the like) may be mounted on the main circuit board 440m and the sub-circuit board 440s. The main circuit board 440m and the sub-circuit board 440s may be referred to as a main board, a printed board assembly (PBA), or a PCB.

The rear housing 450 may be disposed below the circuit board 440 to receive elements of the electronic device 401. The rear housing 450 may form an outer side surface of the electronic device 401. The rear housing 450 may be referred to as rear case or a rear plate. The rear housing 450 may include an area not exposed outside of the electronic device 401 and an area exposed to an outer side surface of the electronic device 401. The area not exposed outside of the electronic device 401 may include a plastic injection product. The area exposed to the outer side surface of the electronic device 401 may be formed of metal. The area exposed to the outer side surface and formed of metal may be referred to as a metal bezel. At least a part of the metal bezel may be utilized as an antenna radiator to transmit and receive a signal having a specified frequency.

The battery 460 may convert chemical energy to electrical energy or electrical energy to chemical energy. The battery 460 may convert chemical energy to electrical energy and may supply the electrical energy to various elements or modules which are mounted above the display device 420 and the circuit board 440. In addition, the battery 460 may convert electrical energy, which is supplied from the outside, to chemical energy and may store the chemical energy therein. The circuit board 440 may include a power management module to manage charging/discharging of the battery 460.

The back cover 470 may be coupled to the rear surface of the electronic device 401. The back cover 470 may be formed of tempered glass, a plastic injection product, and/or metal. The back cover 470 may be implemented integrally with the rear housing 450 or may be implemented to be detachable from the rear housing 450 by a user.

Figure 5A:
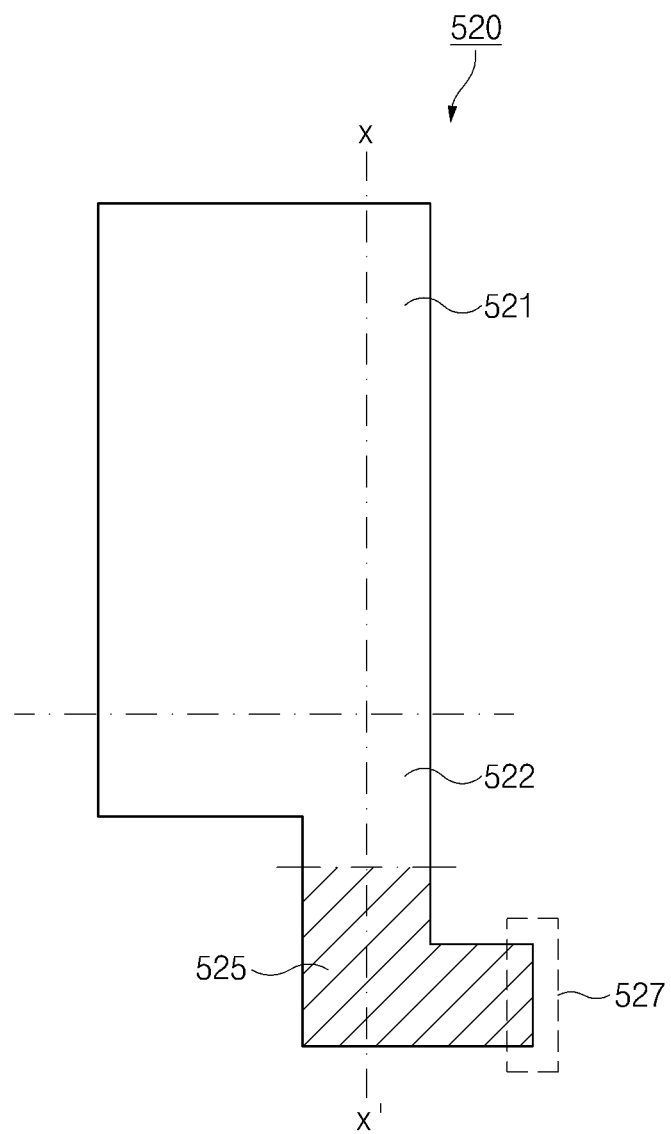
FIGS. 5A and 5B illustrate a display device of an electronic device, according to an embodiment of the present disclosure.
Figure 5B:
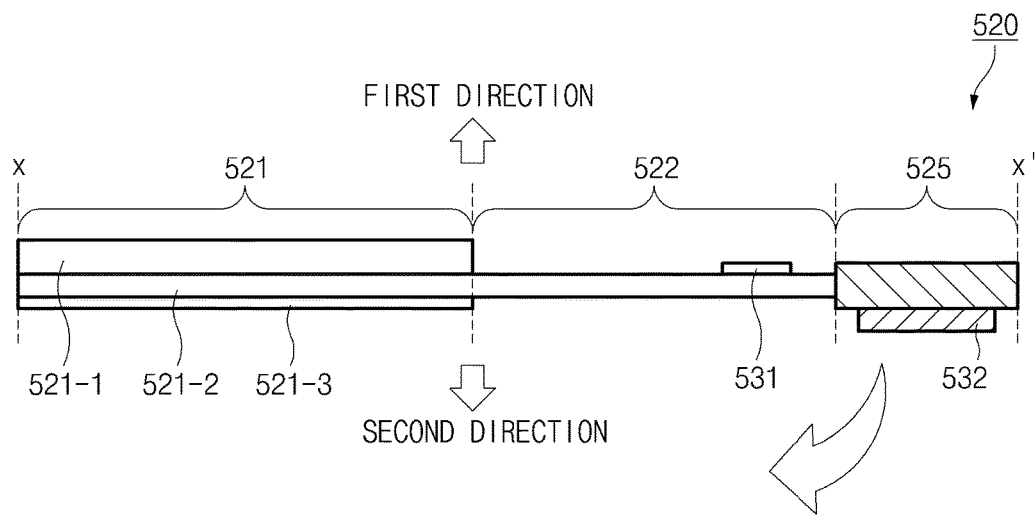

FIGS. 5A and 5B illustrate a display device of an electronic device, according to an embodiment of the present disclosure.

Referring to FIG. 5A, a display device 520 is provided. The display device 520 may include a display area 521, a connecting area 522, and an FPCB 525. The display device 520 may be referred to as a display module or display assembly. Through the display area 521, various types of content (e.g., an image, a text or the like) may be output or displayed, or an input (e.g., a touch or hovering input) may be received from a user. The connecting area 522 may be extended from one side of the display area 521 and may be folded or bent in a specific direction. The FPCB 525 may be electrically connected with a conductive pattern formed above the connecting area 522. A conductive pattern formed in a partial area 527 of the FPCB 525 may be electrically connected with a main circuit board through a specified connector.

Referring to FIG. 5B a sectional surface of the display device 520 taken along auxiliary line x-x' shown in FIG. 5A is provided. As shown in FIG. 5B, a touch screen display panel 521-1, a synthetic film (e.g., polyimide (PI) film) 521-2, and panel/film layer (e.g., a protective film (PF), a back panel, or the like) 521-3 are stacked in the display area 521 of the display device 520. The display panel 521-1 may be disposed on a front surface (first-directional front surface), which faces a first direction, of the synthetic film 521-2 and the panel/film layer 521-3 may be disposed on a rear surface (a second-directional rear surface), which faces a second direction, of the synthetic film 521-2.

Various layers included in the display area 521 may be totally or partially stacked above the connecting area 522 of the display device 520. The connecting area 522 may include the synthetic film 521-2 extended from one side of the display area 521. A hardware module 531 (e.g., a display driver integrated circuit (DDI)) may be disposed on the first-directional front surface of the synthetic film 521-2.

An FPCB 525 may include various conductive patterns formed on a first-directional front surface thereof and/or on a second-directional rear surface thereof. The conductive pattern formed on the front surface and/or the rear surface of the FPCB 525 may be electrically connected with a conductive pattern formed above the connecting area 522. A hardware module (e.g., a biometric sensor or a pressure sensor) 532, which performs a specified function, may be mounted on the second-directional rear surface of the FPCB 525.

A part of the connecting area 522 may be folded toward the second-directional rear surface of the display area 521 such that the second-directional rear surface of the FPCB 525 is apart from the second-directional rear surface of the display area 521 to face the second-directional rear surface of the display area 521 facing the second direction. Accordingly, the module 532 disposed on the rear surface of the FPCB 525 may be disposed below the display area 521.

Figure 6A:
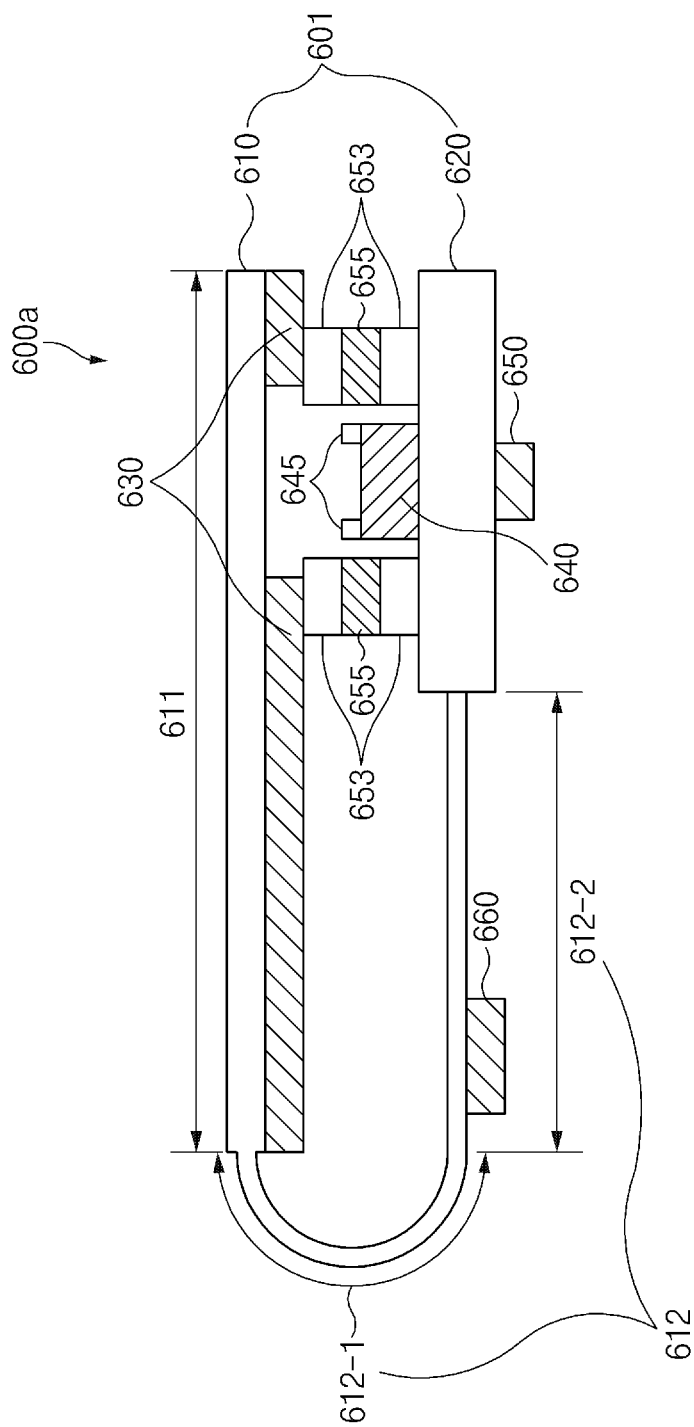
FIGS. 6A and 6B illustrate mounting structures for hardware modules in an electronic device, according to an embodiment of the present disclosure.
Figure 6B:
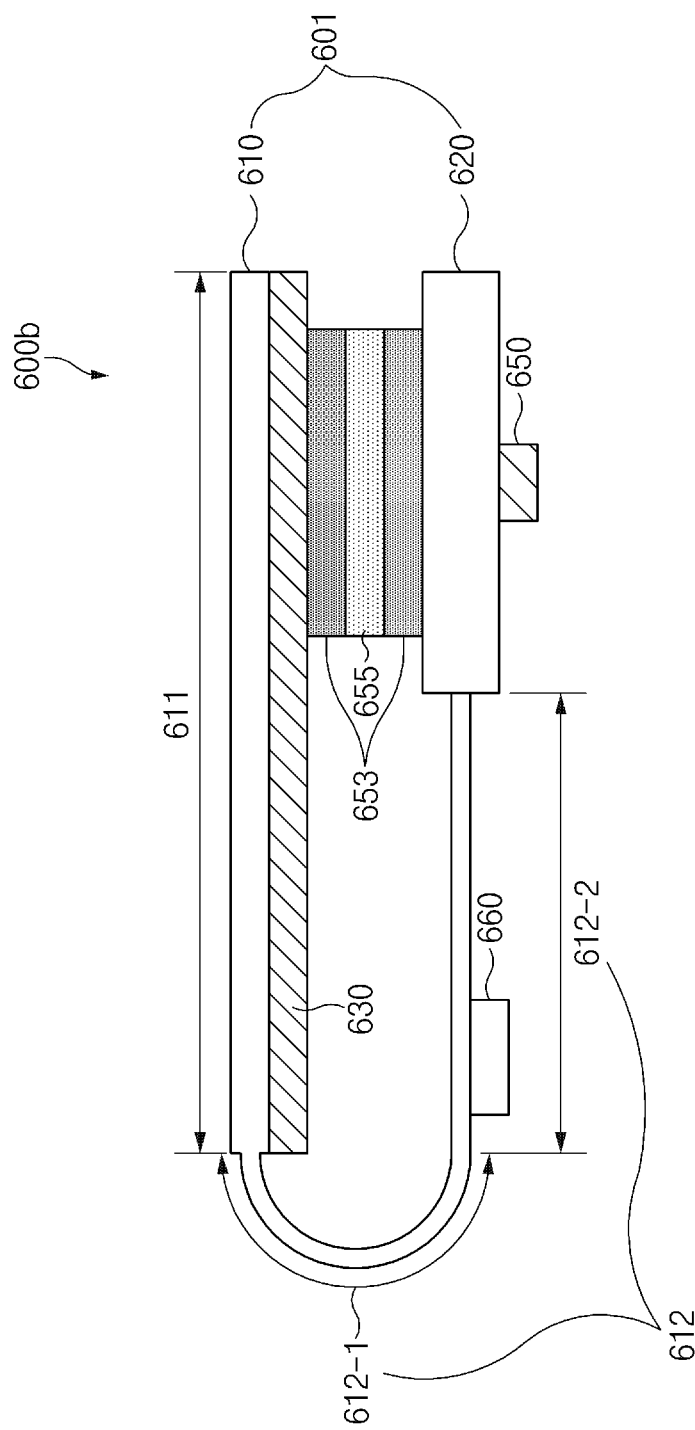

FIGS. 6A and 6B illustrate mounting structures for hardware modules in an electronic device, according to an embodiment of the present disclosure.

Referring to FIG. 6A, an electronic device 600a is provided. The electronic device 600a may include a display 610, an FPCB 620, a back panel 630, a first (hardware) module 640, a buffer member 645, an adhesive layer 653, a pressure sensor 655, a second (hardware) module 650, and a third (hardware) module 660. The display 610 and the FPCB 620 may constitute a display device 601. The electronic device 600a may omit one or more of the elements illustrated in FIG. 6A, and may additionally include one or more elements which are not illustrated in FIG. 6A.

The display 610 may include a display area 611 and a connecting area 612 extended from one side of the display area 611. A bent area 612-1 of the connecting area 612 may be folded toward the rear surface of the display area 611 such that a rear surface of the FPCB 620 is apart from the display area 611 to face the display area 611.

The display area 611 of the display 610 may include a plurality of layers. The layers may include at least one of an adhesive layer, a polarization layer, a display panel and a synthetic film (e.g., PI film) Various contents may be output through a plurality of pixels, which are included in the display panel, in the display area 611.

The connecting area 612 of the display 610 may be folded, such that the first module 640 above the FPCB 620 is apart from the display 610, to face the display 610. As the connecting area 612 is bent, at least a part of the connecting area 612 may have specific curvatures.

The connecting area 612 may include at least one of layers included in the display area 611. The connecting area 612 may include at least a synthetic film. The connecting area 612 may be formed of a PI. Pixels may not be formed in the connecting area 612. Alternatively, the connecting area 612 may include a plurality of pixels to constitute a part of the display panel.

The bent area 612-1 of the connecting area 612 may further include a bending protect layer (BPL) to prevent a bent portion from being broken. The third module 660 (e.g., DDI) may be mounted on one surface (e.g., a front surface or rear surface) of a planar area 612-2 of the connecting area 612.

The FPCB 620 may be electrically connected with the connecting area 612 of the display 610. The first module 640 (e.g., a biometric sensor or a pressure sensor), may be disposed on the rear surface (i.e., a first surface—a surface facing the display area 611 of the display 610) of the FPCB 620. In addition, the second module 650 may be disposed on a front surface (i.e., second surface—a surface opposite to the first surface) of the FPCB 620. The second module 650 (e.g., a biometric sensor IC, a pressure sensor IC, or the like) may be associated with a function of the first module 640.

The back panel (or C-panel) 630 may be formed under the display area 611 of the display 610, i.e., on a rear surface of the display 610. The back panel 630 may include at least one of a light shielding layer (EMBO layer), which is to shield light emitted from the display 610, a buffer layer (e.g., a sponge layer), which is to reduce impact applied onto the display 610 by a user input, a metallic layer (e.g., copper (Cu) or a graphite layer), and an electronic pen sensor layer. An opening may be formed in an area, which corresponds to the first module 640, of the back panel 630, i.e., above the first module 640.

The first module 640 may include various hardware modules which are disposed below the display 610. The first module 640 may include a biometric sensor (e.g., a fingerprint sensor) and/or a pressure sensor. For example, when the first module 640 includes a biometric sensor and a pressure sensor, at least one pressure sensor may be disposed adjacent to the biometric sensor and may be disposed on the rear surface of the FPCB 620 (i.e., a first surface) (see FIGS. 9 and 10). In this case if the pressure sensor detects pressure having a specified value or more, the biometric sensor may be activated (see FIGS. 12 and 13).

The buffer member 645 may be disposed on a surface, which faces the display 610, of the first module 640. The buffer member 645 may prevent the display 610 from pressing the first module 640 as the display 610 is bent by a physical (i.e., a touch) input from a user. The buffer member 645 may be formed of a urethane foam (e.g., Poron™).

The adhesive layer 653 may include a water-proof member to pass air while blocking moisture. An area, which surrounds the opening of the back panel 630, may be attached to the FPCB 620 through the adhesive layer 653. Accordingly, the first module 640 may be sealed by the display 610, an inner surface of the opening formed in the back panel 630, the adhesive layer 653, and the FPCB 620.

The pressure sensor 655 may be interposed between the back panel 630 and the FPCB 620 though the adhesive layer 653. Accordingly, when a physical input is received onto the display 610 from the user, the pressure sensor 655 may detect the pressure of the physical input.

Referring to FIG. 6B, an electronic device 600b is provided. The electronic device 600b may include the display 610, the FPCB 620, the back panel 630, the pressure sensor 655, the second (hardware) module 650, and the third (hardware module) 660. The display 610 and the FPCB 620 may constitute the display device 601. In the following description of FIG. 6B, the details of the same elements assigned with the same reference numerals as those of FIG. 6A may be omitted.

The back panel 630 of the electronic device 600b illustrated in FIG. 6B may have no opening, which is different from the back panel 630 of the electronic device 600a illustrated in FIG. 6A. An element, such as the first module 640 of FIG. 6A, may be omitted below the back panel 630 in the electronic device illustrated in FIG. 6B. The adhesive layers 653 and the pressure senor 655 may be disposed below the back panel 630.

The pressure sensor 655 may be disposed between the back panel 630 and the FPCB 620 though the adhesive layers 653. Accordingly, when a physical input is received onto the display 610 from the user, the pressure sensor 655 may detect the pressure of the physical input.

The electronic device 600b may perform a specific function (the control of functions and operations of elements included in the electronic device 600b) if the pressure sensor 655 detects pressure having a specified value or more.

For example, if a specified value or more is detected by the pressure sensor 655 while the electronic device 600b is operating in a sleep mode (meaning a mode of turning off the display 610 and waiting for the input from a user in a low-power state), the electronic device 600b may activate the display 610 and may output a home screen or a lock screen to the display 610. The electronic device 600b may output a user interface (UI), which is based on the intensity of the pressure detected by the pressure sensor 655, to the display 610.

Figure 7A:
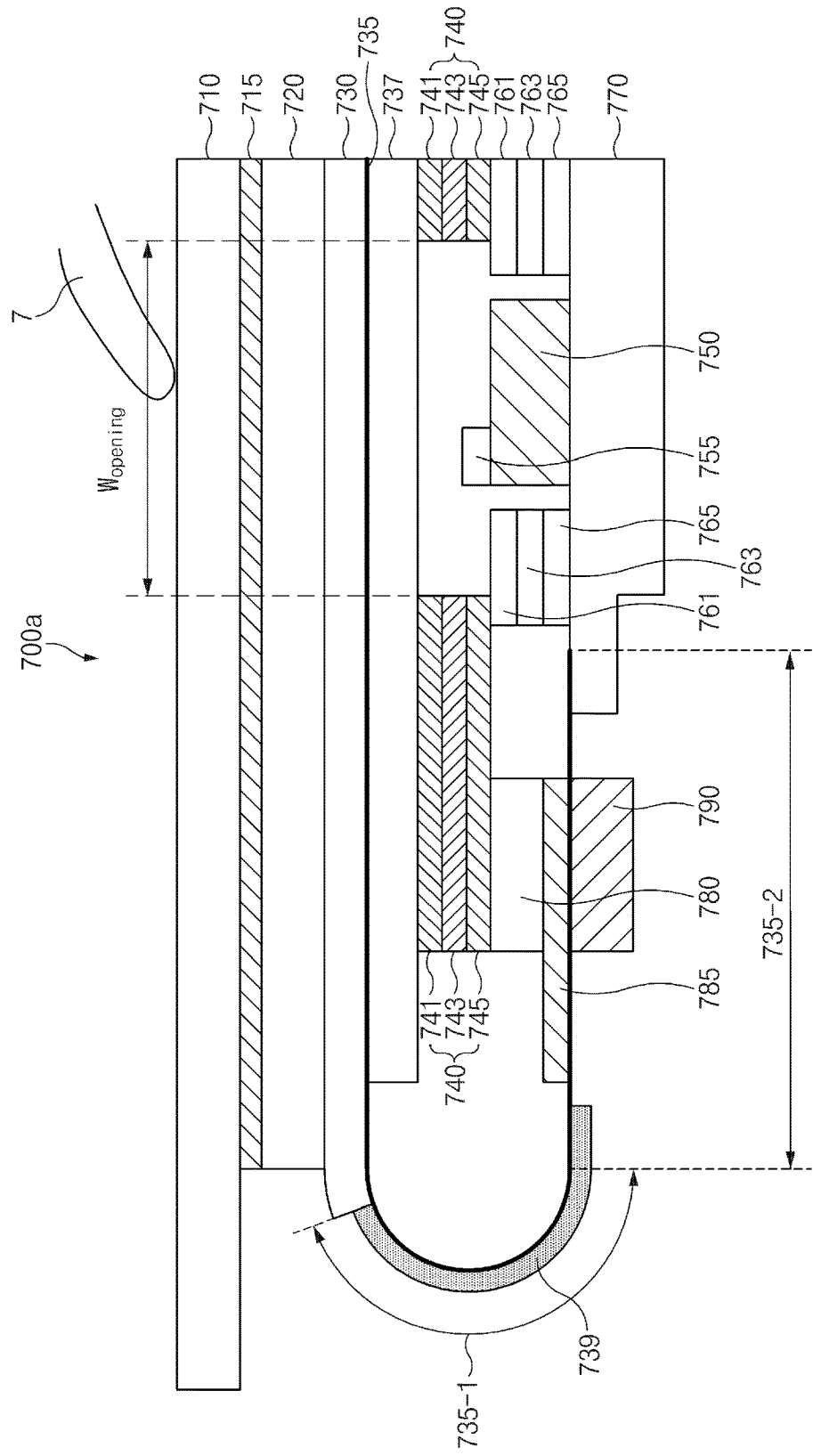
FIGS. 7A and 7B illustrate mounting structures for hardware modules of an electronic device, according to an embodiment of the present disclosure.
Figure 7B:
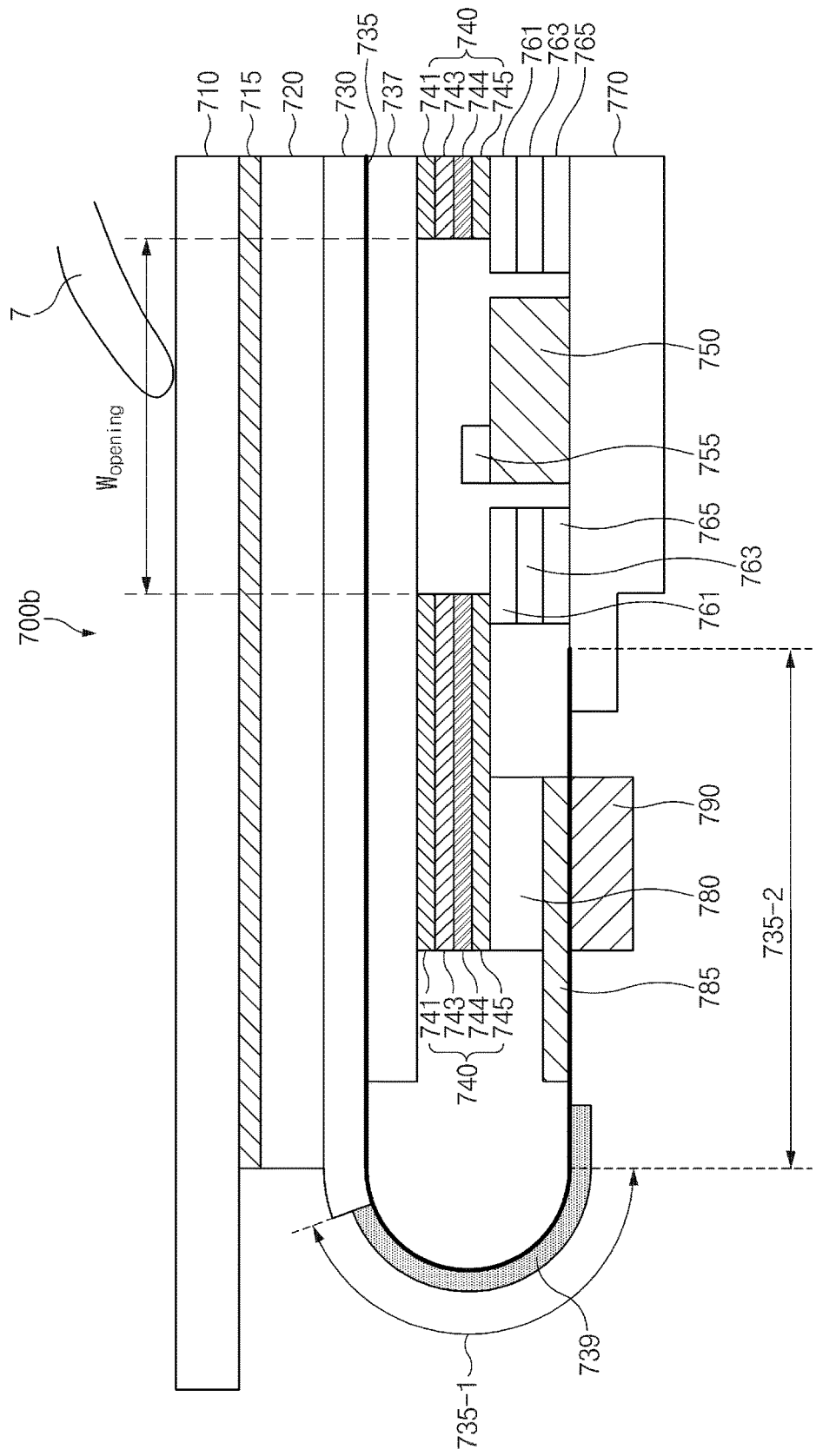

FIGS. 7A and 7B illustrate mounting structures for hardware modules of an electronic device, according to an embodiment of the present disclosure.

Referring to FIG. 7A, an electronic device 700a is provided. The electronic device 700a may include a cover glass 710, an optical clear adhesive (OCA) layer 715, a polarization layer 720, a display panel 730, a PI film 735, a protective film 737, a BPL 739, a back panel 740, a fingerprint sensor 750 (or other biometric sensor), a buffer member 755, adhesive layers 761 and 765, a pressure sensor 763, an FPCB 770, an adhesive layer 780, a protective film 785, and a DDI 790. The OCA layer 715, the polarization layer 720, the display panel 730, the PI film 735, the BPL 739, and the FPCB 770 constitute a display device. In addition, although FIG. 7A illustrates the fingerprint sensor 750 serving as an example of a biometric sensor, this disclosure is not limited thereto. For example, the fingerprint sensor 750 may be substituted with an iris sensor or another biometric sensor.

The cover glass 710 may transmit light generated by the display panel 730. In addition, a user may make a touch contact with the top of the cover glass 710 by a finger 7 of a body.

The OCA layer 715 may be a transparent adhesive layer and may allow the cover glass 710 to adhere to the polarization layer 720.

The polarization layer (or polarization film) 720 may prevent external light from being reflected to improve panel visibility in a bright place. The polarization layer 720 may include a polyethylene terephthalate (PET) film or a tri-acetyl cellulose (TAC) film.

The display panel 730 may include a scan line, a data line, a light emitting device (e.g., OLED), which generates light based on signals supplied from the scan line and the data line, a substrate (e.g., a low temperature poly silicon (LTPS) substrate) above which the light emitting device is disposed, and a thin film encapsulation (TFE) film which protects the light emitting device.

The PI film 735 (i.e., a flexible member) may be disposed below the display panel 730. The PI film 735 may include a wiring for supplying power and/or a signal to the display panel 730. The PI film 735 may include a first area making contact with the display panel 730 and a second area which does not make contact with the display panel 730.

The second area of the PI film 735 may be folded toward the rear surface of the display panel 730. The second area may be divided into a bent area 735-1 and a planar area 735-2. Due to the bent area 735-1, the planar layer 735-2 of the PI film 735 may face the display panel 730, and the fingerprint sensor 750 may be apart from the display panel 730 to face the display panel 730.

The PI film 735 may be disposed above the display panel 730 or may be included as an element in the display panel 730.

The protective film 737 may be disposed below the PI film 735 to support the PI film 735.

The BPL 739 may be attached to the bent area 735-1 and/or at least a part of the planar area 735-2 of the PI film 735. The BPL 739 may prevent the bent area 735-1 from being broken.

The back panel 740 may be formed below the protective film 737 on a rear surface of the display panel 730. The back panel 740 may include at least one of a light shielding layer (e.g., an EMBO layer) 741, a buffer layer (e.g., a sponge layer) 743, and a metallic layer (e.g., a copper (Cu) and graphite layer) 745.

An opening $W_{opening}$ may be formed in an area, which corresponds to the biometric sensor 750, of the back panel 740, that is, above the fingerprint sensor 750. Due to the opening $W_{opening}$, the fingerprint formed in the finger 7 of the user may be recognized by the fingerprint sensor 750. The light generated from the display panel 730 may be reflected from the fingerprint of the finger 7, and the reflected light may reach the fingerprint sensor 750 through the cover glass 710, the OCA layer 715, the polarization layer 720, the display panel 730, the PI film 735, the protective film 737, and the opening $W_{opening}$. In other words, the fingerprint sensor 750 may be configured to use at least one of a plurality of pixels, which are included in the display panel 730, as a light source for fingerprint recognition.

The fingerprint image of the finger 7 may be captured by the fingerprint sensor 750. The fingerprint sensor 750 may correspond to an optical fingerprint sensor. The fingerprint sensor 750 may capture a fingerprint image using an image sensor (e.g., a complementary metal oxide semiconductor (CMOS) or a charge-coupled device (CCD)) embedded therein. The fingerprint sensor 750 may extract unique fingerprint minutiae from the fingerprint image. The fingerprint minutiae may include, for example, a ridge ending, a crossover, a bifurcation, a pore, and the like, included in the fingerprint. The fingerprint minutiae may be compared with fingerprint minutiae registered in advance, such that the fingerprint minutiae are used for user authentication.

The buffer member 755 may be disposed on the surface of the fingerprint sensor 750. The buffer member 755 may prevent the protective film 737 from pressing the fingerprint sensor 750 due to a physical input from the finger 7 of the user. The buffer member 755 may be formed of a urethane foam (e.g., Poron™).

The adhesive layers 761 and 765 may include a member through which air may pass while blocking moisture. The pressure senor 763 may be disposed between the adhesive layers 761 and 765. The pressure sensor 763 may detect pressure applied by the finger 7 of the user and transmitted through the cover glass 710, the OCA layer 715, the polarization layer 720, the display panel 730, the PI film 735, the protective film 737, the back panel 740, and the adhesive layer 761.

An area that surrounds the opening $W_{opening}$ of the back panel 740 may be attached to the FPCB 770 through the adhesive layer 761, the pressure sensor 763, and the adhesive layer 765. Accordingly, the fingerprint sensor 750 may be sealed by the protective film 737, an inner surface of the opening formed in the back panel 740, the adhesive layer 761, the pressure sensor 763, the adhesive layer 765, and the FPCB 770.

The FPCB 770 may be electrically connected with the planar area 735-2 of the PI-film 735. The FPCB 770 may be electrically connected with the conductive pattern formed in the PI-film 735. The fingerprint sensor 750 may be disposed on one surface of the FPCB 770. A driver IC of the fingerprint sensor 750 may be disposed on another surface of the FPCB 770.

The adhesive layer 780 and the protective film 785 may be attached between the back panel 740 and the PI film 735 to physically support the cover glass 710, the OCA layer 715, the polarization layer 720, the display panel 730, the PI film 735, and the protective film 737.

The DDI 790 may control the display panel 730. The DDI 790 may supply the display panel 730 with an image signal corresponding to image data received from the processor (i.e., a host) at a preset frame rate. The DDI 790 may be disposed on one surface of the planar area 735-2 of the PI film 735.

Referring to FIG. 7B, an electronic device 700b is provided. The electronic device 700b may include elements which are the same as or similar to those of the electronic device 700a illustrated in FIG. 7A. In the following description of FIG. 7B, the details of the same elements assigned with the same reference numerals as those of FIG. 7A may be omitted in order to avoid redundancy.

The back panel 740 may further include an electronic pen sensor layer 744 in addition to the light shielding layer 741, the buffer layer 743, and the metallic layer 745. The electronic pen sensor layer 744 may be used to sense a contact state and a contact position by an electronic pen (e.g., a position indicator, a stylus, a digitizer pen, or the like). The electronic pen sensor layer 744 may be referred to as electronic pen sensor sheet or a digitizer.

FIG. 7B illustrates the electronic pen sensor layer 744 interposed between the buffer layer 743 and the metallic layer 745, but this disclosure is not limited thereto. The electronic pen sensor layer 744 may be interposed between the light shielding layer 741 and the buffer layer 743, and may be interposed between the light shielding layer 741 and the protective film 737.

Figure 8A:
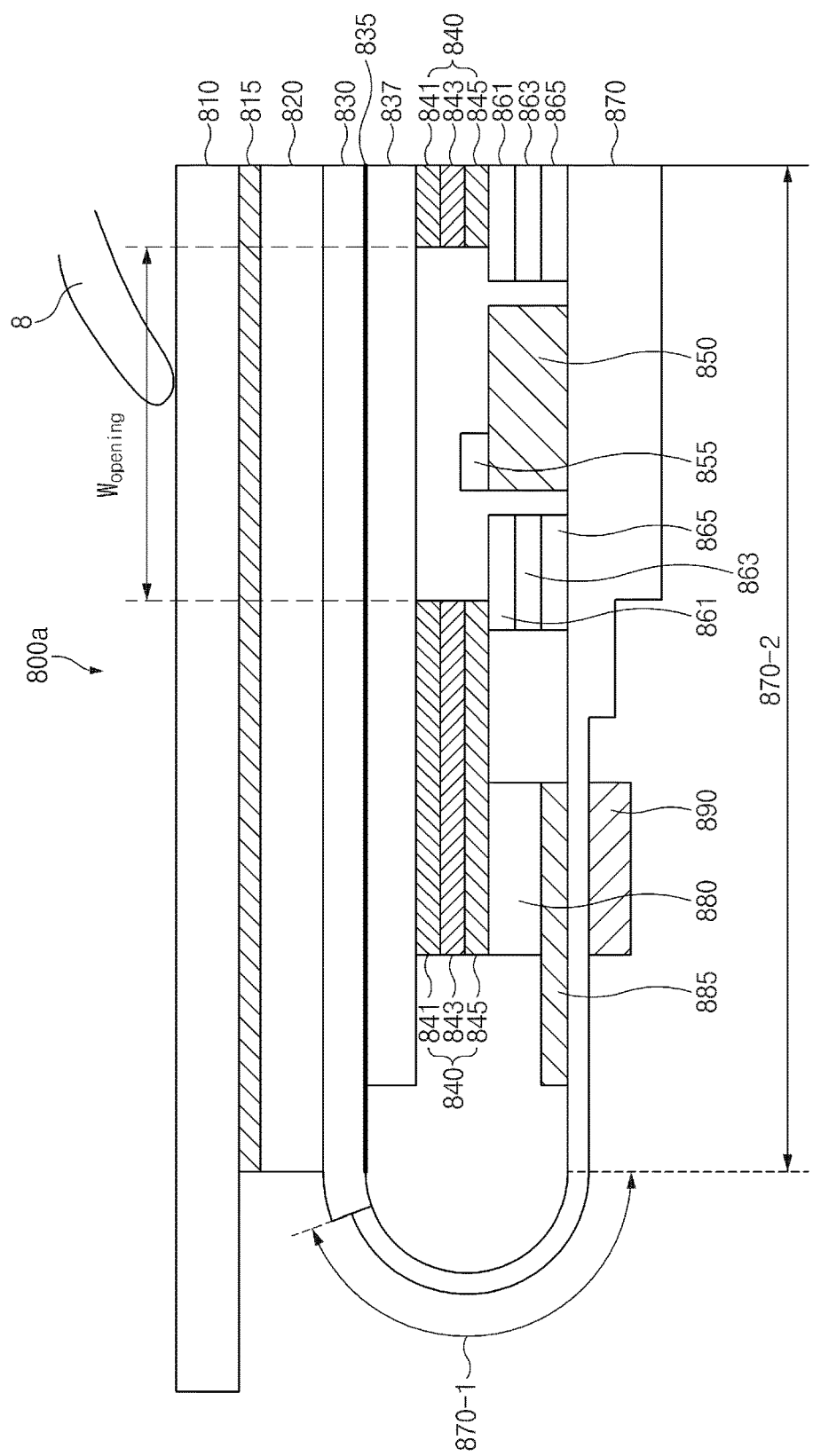
FIGS. 8A and 8B illustrate mounting structures for hardware modules of an electronic device, according to an embodiment of the present disclosure.
Figure 8B:
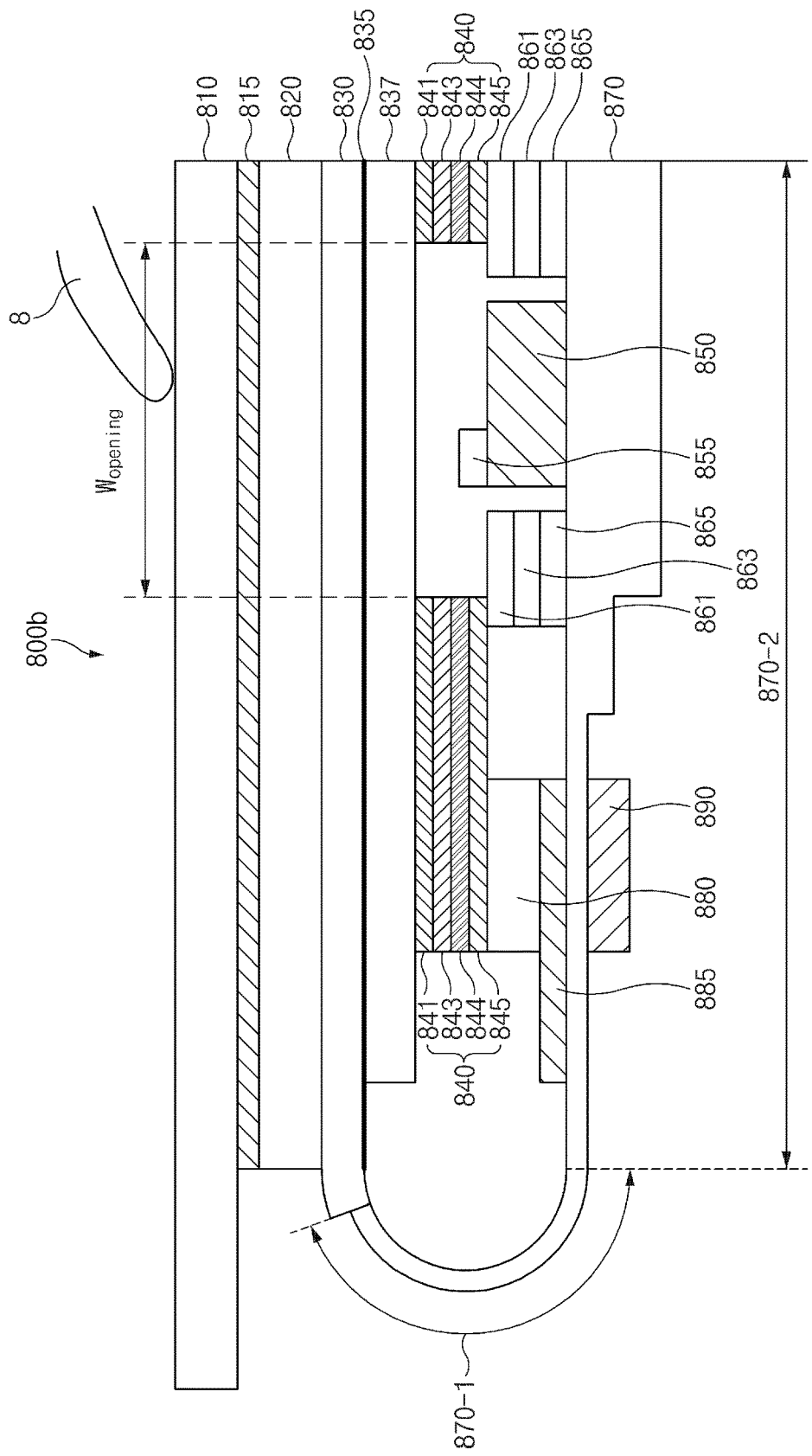

FIGS. 8A and 8B illustrate mounting structures for hardware modules of an electronic device, according to an embodiment of the present disclosure.

Referring to FIG. 8A, an electronic device 800a is provided. The electronic device 800a may include a cover glass 810, an OCA layer 815, a polarization layer 820, a display panel 830, a PI film 835, a protective film 837, a back panel 840, a fingerprint sensor 850, a buffer member 855, adhesive layers 861 and 865, a pressure sensor 863, an FPCB 870, an adhesive layer 880, a protective film 885, and a DDI 890. The OCA layer 815, the polarization layer 820, the display panel 830, the PI film 835, the BPL 739, and the FPCB 870 constitute a display device. In addition, although FIG. 8A illustrates the fingerprint sensor 850 serving as an example of a biometric sensor, this disclosure is not limited thereto. For example, the fingerprint sensor 850 may be substituted with an iris sensor or another biometric sensor. In the following description of FIG. 8A, the details of the same elements assigned with the similar reference numerals as those of FIG. 7A may be omitted.

The FPCB 870 may be electronically connected with the display panel 830. The FPCB 870 may be electrically connected with the display panel 830 through a hot bar or soldering.

The FPCB 870 may include a bent area 870-1 and a planar area 870-2 connected with the bent area 870-1. The bent area 870-1 may be connected with the display panel 830 and may be folded toward a rear surface of the display panel 830. In FIG. 8A, the FPCB 870 may be folded, which is different from the FPCB 770 of FIG. 7A.

The rear surface of the planar area 870-2 of the FPCB 870 may be apart from a rear surface of the display panel 830 to face the rear surface of the display panel 830 due to the bent area 870-1 of the FPCB 870. Accordingly, the fingerprint sensor 850 and the pressure sensor 863 may be apart from the display panel 830 to face the display panel 830.

The fingerprint sensor 850 and at least one pressure sensor 863 adjacent to the fingerprint sensor 850 may be disposed on the rear surface (i.e., a first surface—a surface facing the display panel 830) of the planar area 870-2 of the FPCB 870. The pressure sensor 863 may be attached to the rear surface of the planar area 870-2 of the FPCB 870 through the adhesive layer 865. The DDI 890 may be disposed on the front surface (i.e., a second surface—an opposite surface to a surface having the protective film 885 attached thereto) of the planar area 870-2 of the FPCB 870.

Referring to FIG. 8B an electronic device 800b is provided. The electronic device 800b illustrated in FIG. 8B may include elements the same as or similar to those of the electronic device 800a illustrated in FIG. 8A. In the following description of FIG. 8B, the details of the same elements assigned with the same reference numerals as those of FIG. 8A may be omitted in order to avoid redundancy.

The back panel 840 may further include an electronic pen sensor layer 844 in addition to a light shielding layer 841, a buffer layer 843, and a metallic layer 845. The electronic pen sensor layer 844 may be used to detect a contact state by an electronic pen and a contact position of the electronic pen. FIG. 8B illustrates the electronic pen sensor layer 844 interposed between the buffer layer 843 and the metallic layer 845, but this disclosure is not limited thereto. The electronic pen sensor layer 844 may be interposed between the light shielding layer 841 and the buffer layer 843, and may be interposed between the light shielding layer 841 and the protective film 837.

Figure 9:
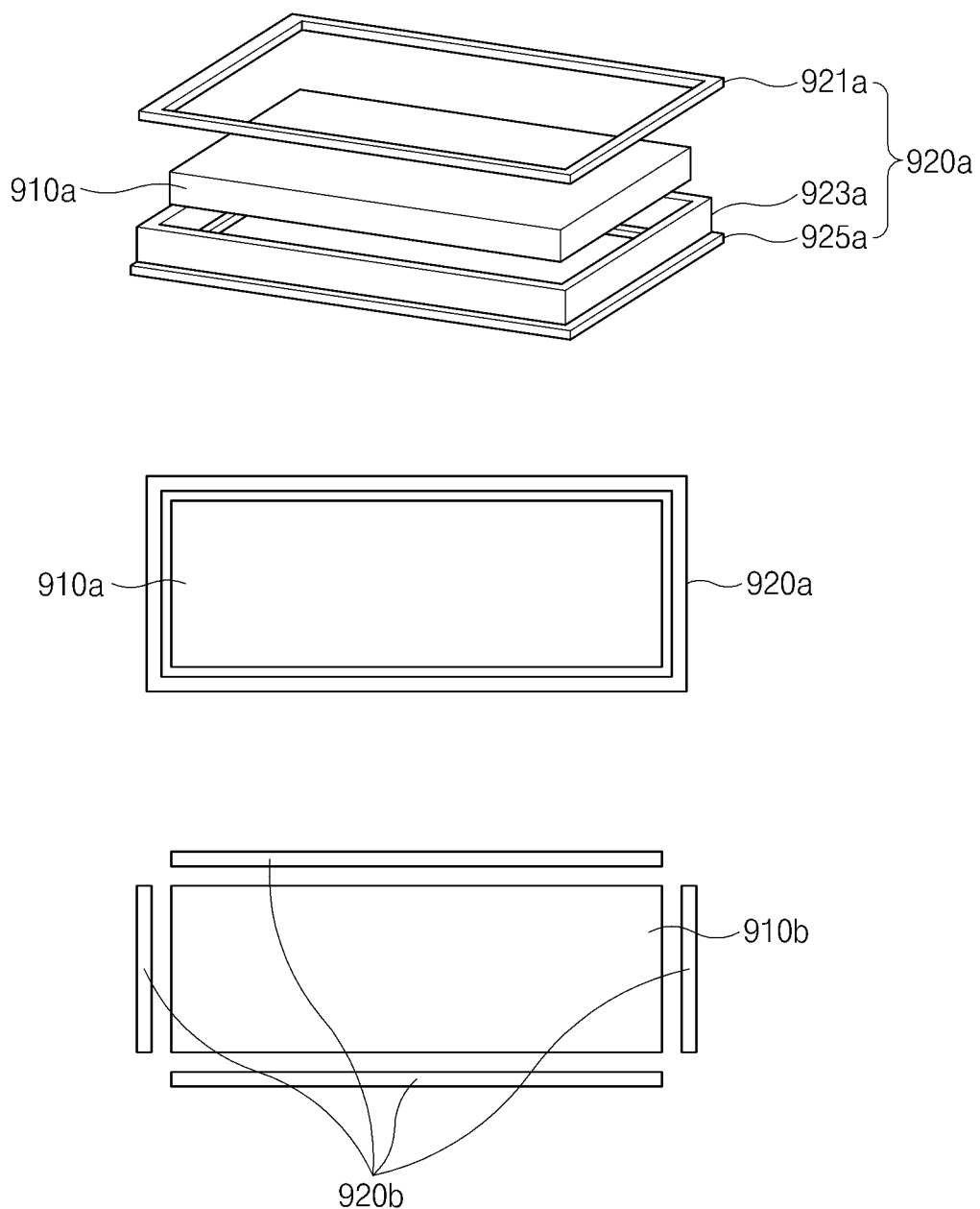
FIG. 9 illustrates a mounting structure for a biometric sensor and a pressure sensor, according to an embodiment of the present disclosure.

FIG. 9 illustrates a mounting structure for a biometric sensor and a pressure sensor, according to an embodiment of the present disclosure.

Referring to FIG. 9, a pressure sensor 920a may be disposed to surround a biometric sensor (e.g., a fingerprint sensor) 910a. The pressure sensor 920a may include a first electrode 921a, a second electrode 925a, and a dielectric layer 923a. The pressure sensor 920a may sense the pressure of the touch based on capacitance between the first electrode 921a and the second electrode 925a, which varies by the touch.

The first electrode 921a and/or the second electrode 925a may be implemented to be transparent or opaque. For example, if implemented to be opaque, the first electrode 921a and/or the second electrode 925a may include copper (Cu), silver (Ag), magnesium (Mg), titanium (Ti), or opaque graphene. In addition, if the first electrode 921a and/or the second electrode 925a is implemented to be transparent, the first electrode 921a and/or the second electrode 925a may be formed of indium thin oxide (ITO), indium zinc oxide (IZO), Ag nanowire, metal mesh, transparent conducting polymer, or transparent graphene.

The dielectric layer 923a may be implemented with a dielectric substance having resilience, for example, a silicone foam, silicone membrane, sponge, rubber, polycabondate (PC), or polyethylene terephthalate (PET).

Alternatively, a pressure sensor 920b may be disposed to surround a biometric sensor 910b and may be divided into a plurality of pressure sensors (e.g., four pressure sensors). In this case, the pressure sensor 920b may detect the position distribution of applied pressure as well as the intensity of the pressure.

Figure 10:
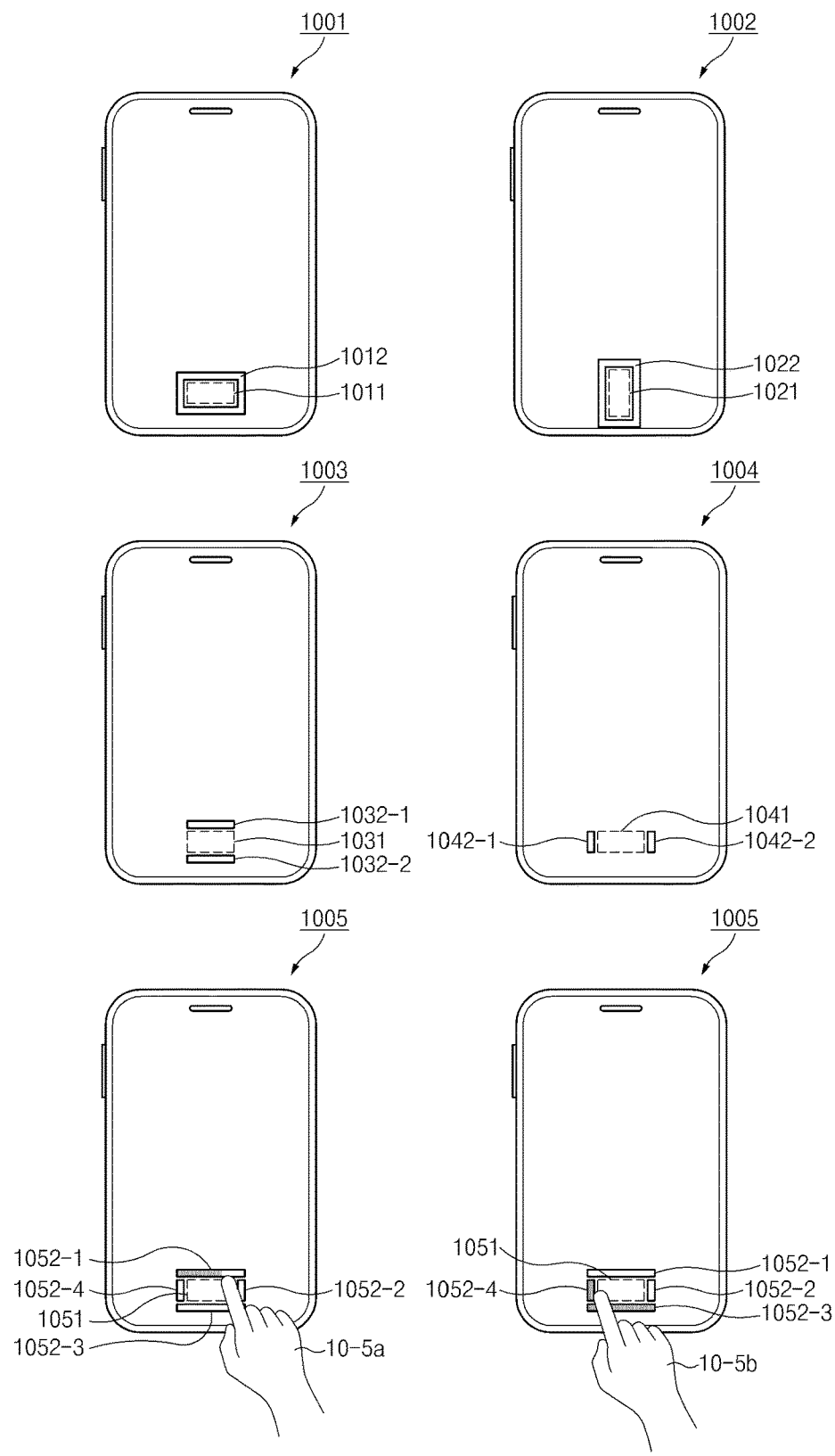
FIG. 10 illustrates mounting structures for biometric sensors and pressure sensors, according to an embodiment of the present disclosure.

FIG. 10 illustrates mounting structures for biometric sensors and pressure sensors, according to an embodiment of the present disclosure.

Referring to FIG. 10, electronic devices 1001, 1002, 1003, 1004, and 1005 are provided. Referring to electronic device 1001, a pressure sensor 1012 may be disposed to surround a biometric sensor (e.g., a fingerprint sensor) 1011. The biometric sensor 1011 may have a rectangular shape in which a width side is longer than a length side. The pressure sensor 1012 may include a single first electrode, a single second electrode, and a dielectric layer (see FIG. 9).

Referring to electronic device 1002, a pressure sensor 1022 may be disposed to surround a biometric sensor (e.g., a fingerprint sensor) 1021. The biometric sensor 1021 may have a rectangular shape in which a length side is longer than a width side.

Referring to electronic device 1003, two pressure sensors 1032-1 and 1032-2 may be disposed adjacent to an upper width side and a lower width side, respectively, of a biometric sensor (e.g., fingerprint sensor) 1031.

Referring to electronic device 1004, two pressure sensors 1042-1 and 1042-2 may be disposed adjacent to a left length side and a right length side, respectively, of a biometric sensor (e.g., fingerprint sensor) 1041.

Referring to electronic device 1005 four pressure sensors 1052-1, 1052-2, 1052-3, and 1052-4 may be disposed adjacent to each of four sides, respectively, of a biometric sensor (e.g., fingerprint sensor) 1051. For example, a finger 10-5a of a user may touch with a specified pressure, i.e., a force touch, around an upper end of the biometric sensor 1051. In this case, the electronic device 1005 may recognize the force touch made by the finger 10-5a through the upper pressure sensor 1052-1 and the right pressure sensor 1052-2 disposed at the right side. Alternatively, a finger 10-5b of a user may make a force touch near a lower left end of the biometric sensor (e.g., fingerprint sensor) 1051. In this case, the electronic device 1005 may recognize the force touch made by the finger 10-5b through the lower pressure sensor 1052-3 and the left pressure sensor 1052-4. According to the electronic device 1005, the force touch by the finger 10-5a and the force touch by the finger 10-5b may be recognized as different inputs. Accordingly, a function corresponding to each input may be provided.

Figure 11A:
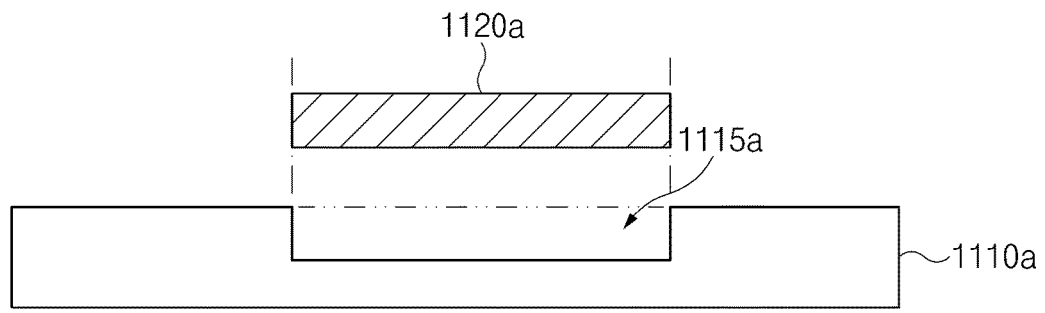
FIGS. 11A and 11B illustrates flexible printed circuit board (FPCB) mounting structures for biometric sensors and pressure sensors, according to an embodiment of the present disclosure.
Figure 11B:
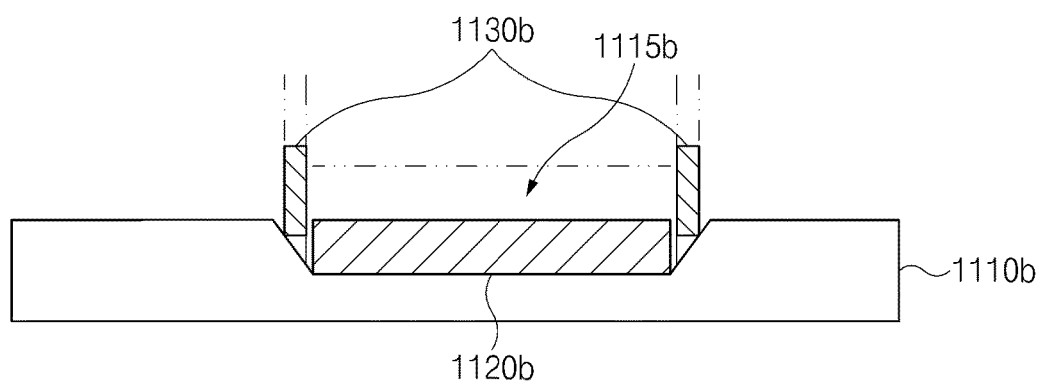

FIGS. 11A and 11B illustrates flexible printed circuit board (FPCB) mounting structures for biometric sensors and pressure sensors, according to an embodiment of the present disclosure;

Referring to FIG. 11A, a biometric sensor (e.g., a fingerprint sensor) 1120a may be disposed on one surface of an FPCB 1110a. The biometric sensor 1120a may correspond to the first module 640 illustrated in FIG. 6A, the fingerprint sensor 750 illustrated in FIG. 7A, or the fingerprint sensor 850 illustrated in FIG. 8A. The FPCB 1110a may correspond to the FPCB 620 illustrated in FIG. 6A, the FPCB 770 illustrated in FIG. 7A, or the FPCB 870 illustrated in FIG. 8A. A recessed portion 1115a may be formed in one surface of the FPCB 1110a through an etching process. The biometric sensor 1120a may be seated in the recessed portion 1115a.

Referring to FIG. 11B, a biometric sensor (e.g., a fingerprint sensor) 1120b and a plurality of pressure sensors 1130b may be provided in one surface of an FPCB 1110b. The pressure sensors 1130b may correspond to the pressure sensor 655 illustrated in FIG. 6A, the pressure sensor 763 illustrated in FIG. 7A, or the pressure sensor 863 illustrated in FIG. 8A. Adhesive layers (e.g., tapes) may be additionally attached to front and rear surfaces of the pressure sensors 1130b. A recessed portion 1115b may be formed in one surface of the FPCB 1110b. The biometric sensor 1120b and the pressure sensors 1130b may be seated in the recessed portion 1115b formed in the FPCB 1110b.

The thicknesses of the FPCB 1110a and 1110b, having the biometric sensors 1120a and 1120b disposed therein, may be reduced due to the recessed portions 1115a and 1115b formed in the FPCB 1110a and 1110b, respectively.

Figure 12:
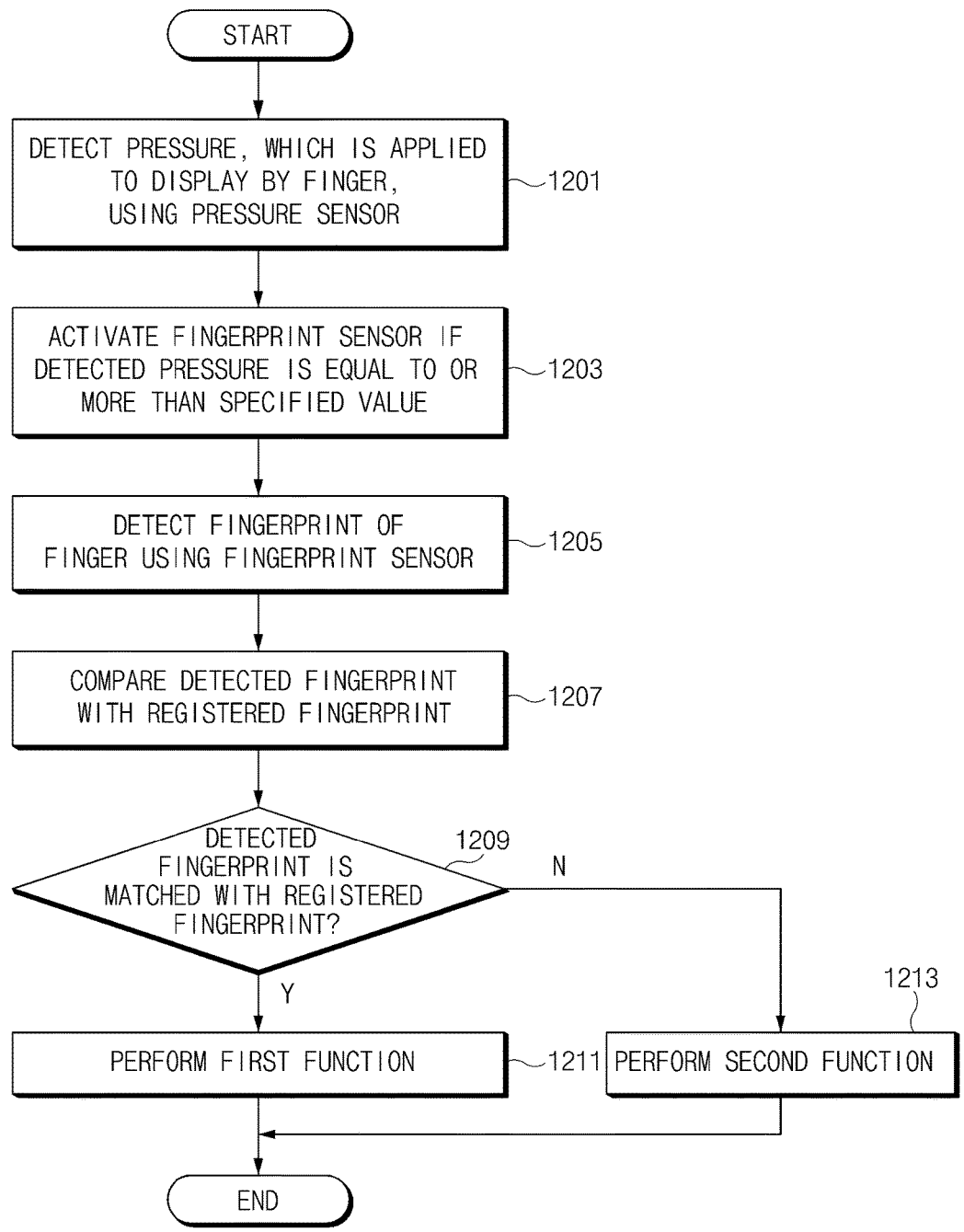
FIG. 12 is a flowchart of a fingerprint verification method, according to an embodiment of the present disclosure.

FIG. 12 is a flowchart of a fingerprint verification method, according to an embodiment of the present disclosure.

Referring to FIG. 12, a fingerprint verification method is described. The fingerprint verification method may be implemented with instructions that are performed (or executed) by a processor of an electronic device. The instructions may be stored in computer recording media or internal/external memory of the electronic device.

In operation 1201, the electronic device may detect pressure applied to a part (e.g., an area on which the guide image 315 representing a home button is displayed as illustrated in FIG. 3) of a display (or a cover glass) by a finger of a user through the pressure sensor. The electronic device may detect pressure applied by the finger regardless of the ON/OFF states of the display panel of the display.

In operation 1203, the electronic device may activate a fingerprint sensor (or other biometric sensor) if the pressure detected in operation 1201 is more than or equal to a specified value. In other words, if the force touch is received from the user, the fingerprint sensor and a fingerprint sensor IC driving the same may be triggered to operate.

In operation 1205, the electronic device may detect the fingerprint (i.e., fingerprint minutiae) of a finger using the fingerprint sensor. For example, in the case that the fingerprint sensor corresponds to an optical fingerprint sensor, light having specified brightness may be emitted from a part (e.g., an area on which the guide image 315 representing a home button is displayed, as illustrated in FIG. 3) of the display corresponding to an area for the fingerprint sensor to increase the accuracy of the fingerprint verification.

In operation 1207, the electronic device may compare the fingerprint detected in operation 1205, to a fingerprint which is stored in the memory or registered in a server.

In operation 1209, the electronic device may determine whether the fingerprint compared in operation 1207 is matched with the registered fingerprint. If the detected fingerprint is matched with the registered fingerprint in operation 1209, the electronic device may perform a first function in operation 1211. For example, if the display is in an OFF state when operation 1201 is performed, the first function may include a function of switching the state of the display state to an ON state. In this case, the first function may further include a function of outputting an unlocked screen onto the display. Alternatively, if the display is in the ON state and a locked screen is output onto the display at the time when operation 1201 is performed, the first function may include a function of outputting an unlocked screen to the display.

If the detected fingerprint is not matched with the registered fingerprint in operation 1209, the electronic device may perform a second function in operation 1213. For example, the electronic device may perform the second function different from the first function. For example, if the display is in the OFF state at the time when operation 1201 is performed, the second function may include a function of maintaining the display in the OFF state. Alternatively, if the display is in the ON state and a locked screen is output onto the display at the time when operation 1201 is performed, the second function may include a function of maintaining the locked screen.

Accordingly, if a touch (i.e., a force touch) having a specified value or more is detected through the pressure sensor of the electronic device, the fingerprint sensor is activated to verify the fingerprint of the finger making the touch. Accordingly, the pressure sensor may be actually used as a home button, and the fingerprint of the finger applying pressure to the pressure sensor may be instantly verified, thereby improving the convenience of a user.

Figure 13:
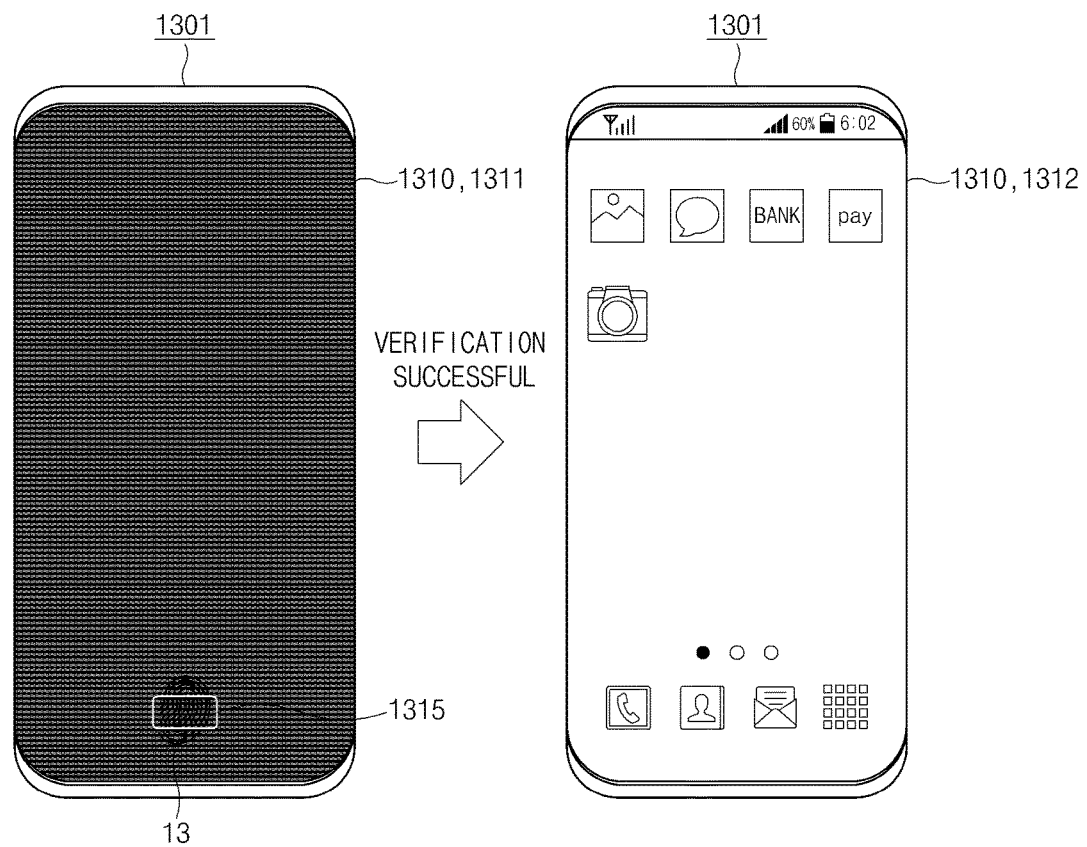
FIG. 13 illustrates a fingerprint verification method, according to an embodiment of the present disclosure.

FIG. 13 illustrates a fingerprint verification method, according to an embodiment of the present disclosure.

Referring to FIG. 13, an electronic device 1301 is provided. A screen 1311 including a guide image 1315 representing a home button may be output to a display 1310 (i.e., a touch screen) of the electronic device 1301. The guide image 1315 may be substantially always output to the display 1310 (i.e., always-on).

For example, a user may make a force touch to an area of the display 1310, onto which the guide image 1315 is output. If a force touch 13 is made on the display 1310, the electronic device 1301 may activate the fingerprint sensor based on the pressure of the force touch 13. The fingerprint of a finger making the force touch 13 may be detected by the activated fingerprint sensor. The electronic device 1301 may compare the detected fingerprint with a registered fingerprint stored in the memory.

For example, if the detected fingerprint is matched with the registered fingerprint (that is, if the fingerprint verification is successful), the electronic device 1301 may switch the state of the display 1310 to the ON state, and may output a home screen 1312, which is unlocked, onto the display 1310 as a first function.

On the other hand, if the detected fingerprint is not matched with the registered fingerprint (that is, if the fingerprint verification is failed), the electronic device 1301 may continuously output the existing screen 1311 as a second function. The electronic device 1301 may temporarily output a warning notice that the detected fingerprint is not matched with the registered fingerprint, if the fingerprint verification is failed.

In general, a fingerprint sensor is disposed above a physical button (e.g., a home button). However, according to an electronic device of the present invention, in the mounting structure for the hardware module in the electronic device, the fingerprint sensor and the pressure sensor may be disposed below the display area of the display. Accordingly, in the case that the function of the physical button is allocated to the pressure sensor and the fingerprint sensor is disposed adjacent to the pressure sensor, even if the display constitutes the entire front surface of the electronic device, an existing function of a home button may be maintained.

According to an embodiment of the present application, an electronic device may include a display including a display area and a connecting area extended from one side of the display area, an FPCB electrically connected with the connecting area, and a first module mounted on a first surface of the FPCB. The connecting area may be bent such that the first module is apart from the display to face the display.

The connecting area may include polyimide (PI). Pixels of the display are not formed in the connecting area.

The connecting area may include a part of a display panel of the display.

At least a part of the connecting area may be bent with a specified curvature.

The electronic device may further include a second module mounted on a second surface of the FPCB, which is opposite to the first surface.

The second module may be configured to operate in association with a function of the first module.

The electronic device may further include a back panel formed on a rear surface of the display, and an opening may be formed in an area of the back panel, which corresponds to the first module.

An area of the back panel, which surrounds the opening, may be attached to the FPCB through an adhesive layer, and the adhesive layer may include a water-proof member which passes air while blocking moisture.

The display may include a back panel formed on a rear surface thereof. An opening may not be formed in the back panel, and the first module may be a pressure sensor.

The first module may include a biometric sensor or a pressure sensor.

The biometric sensor may be configured to use at least one of a plurality of pixels, which are included in the display, as a light source.

The first module may be a biometric sensor, and at least one pressure sensor may be mounted on the first surface while being adjacent to the first module.

The biometric sensor may be configured to be activated if the at least one pressure sensor detects pressure having a specific value or more.

A buffer member may be disposed on a surface of the first module, which faces the display.

The electronic device may further include a display driver integrated circuit mounted on one surface of the connecting area to control the display.

According to an embodiment, the electronic device may include an FPCB including a planar area and a bent area, a sensor mounted on a first surface of the planar area, and a display connected with the bent area. The bent area may be bent such that the sensor is apart from the display to face the display.

The electronic device may further include a back panel formed on a rear surface of the display. An opening may be formed in an area of the back panel, which corresponds to the sensor.

The sensor may be configured to use at least one of a plurality of pixels, which are included in the display, as a light source.

The electronic device may further include a display driver integrated circuit mounted on one surface of the planar area to operate the display.

According to an embodiment, an electronic device may include a display panel having a plurality of pixels to display content, a flexible member including a first area making contact with one surface of the display panel and a second area extended from the one surface of the display panel, a display driver integrated circuit provided above the second area of the flexible member, an FPCB electrically connected with the second area, and a biometric sensor mounted on one surface of the FPCB.

The biometric sensor may be configured to use at least one of a plurality of pixels, which are included in the display, as a light source.

The second area may be bent such that the biometric sensor is apart from the display to face the display.

According to an embodiment, an electronic device may include a display including a display area and a connecting area extended from one side of the display area and a flexible printed circuit board (FPCB) electrically connected with the connecting area. A part of the connection area is folded toward a rear surface of the display area such that a rear surface of the FPCB is apart from the rear surface of the display area to face the rear surface of the display area. A first module is mounted on the rear surface of the FPCB.

According to an embodiment, an electronic device may include a display panel and an FPCB which includes a bent area electrically connected with the display panel and a planar area connected with the bent area. The bent area may be folded toward a rear surface of the display such that a rear surface of the planar area is apart from the rear surface of the display panel to face the rear surface of the display panel. A first module may be mounted on the rear surface of the planar area.

The term "module" used in this disclosure may represent a unit including one or more combinations of hardware, software and firmware. The term "module" may be interchangeably used with the terms "unit", "logic", "logical block", "component" and "circuit". The "module" may be a minimum unit of an integrated component or may be a part thereof. The "module" may be a minimum unit for performing one or more functions or a part thereof. The "module" may be implemented mechanically or electronically. The "module" may include at least one of an application-specific IC (ASIC) chip, a field-programmable gate array (FPGA), and a programmable-logic device for performing some operations, which are known or will be developed.

At least a part of an apparatus (e.g., modules or functions thereof) or methods (e.g., operations) of the present disclosure may be implemented by instructions stored in a computer-readable storage media in the form of a program module. The instruction, when executed by the processor 120, may cause the processor 120 to perform a function corresponding to the instruction. The computer-readable storage media may be the memory 130.

A computer-readable recording medium may include a hard disk, a floppy disk, a magnetic medium (e.g., a magnetic tape), an optical medium (e.g., a CD-ROM and a DVD), a magneto-optical medium (e.g., a floptical disk), and a hardware device (e.g., a read only memory (ROM), a random access memory (RAM), or a flash memory). Also, a program instruction may include not only a mechanical code generated by a compiler, but also a high-level language code executable on a computer using an interpreter. The above hardware unit may be configured to operate via one or more software modules for performing an operation of the present disclosure, and vice versa.

A module or a program module may include at least one of the above elements, or a part of the above elements may be omitted, or additional other elements may be further included. Operations performed by a module, a program module, or other elements may be executed sequentially, in parallel, repeatedly, or in a heuristic method. In addition, some operations may be executed in different sequences or may be omitted. Alternatively, other operations may be added.

While the present disclosure has been shown and described with reference to various embodiments, it will be understood by those skilled in the art that various changes in form and details may be made therein without departing from the spirit and scope of the present disclosure, which is defined, not by the detailed description and embodiments, but by the appended claims and their equivalents.

What is claimed is:

1. An electronic device comprising:
   a display including a display area and a connecting area extending from one side of the display area;
   a flexible printed circuit board (FPCB) connected with the connecting area;
   a first module mounted on a first surface of the FPCB; and
   a back panel formed on a rear surface of the display,
   wherein the connecting area is bent such that the first module is apart from the display to face the display, and
   wherein an opening is formed in an area of the back panel, which corresponds to the first module.

2. The electronic device of claim 1, wherein the connecting area includes polyimide (PI), and wherein pixels of the display are not formed in the connecting area.

3. The electronic device of claim 1, wherein the connecting area includes a part of a display panel of the display.

4. The electronic device of claim 1, wherein at least a part of the connecting area is bent with a specified curvature.

5. The electronic device of claim 1, further comprising:
   a second module mounted on a second surface of the FPCB, which is opposite to the first surface.

6. The electronic device of claim 1, wherein the back panel includes an electronic pen sensor layer.

7. The electronic device of claim 1, wherein an area of the back panel, which surrounds the opening, is attached to the FPCB through an adhesive layer, and
   wherein the adhesive layer includes a water-proof member which passes air and blocks moisture.

8. The electronic device of claim 1,
   wherein the first module is a pressure sensor.

9. The electronic device of claim 1, wherein the first module includes at least one of a biometric sensor and a pressure sensor.

10. The electronic device of claim 9, wherein the biometric sensor is configured to use at least one of a plurality of pixels, which are included in the display, as a light source.

11. The electronic device of claim 1, wherein the first module is a biometric sensor, and
    wherein at least one pressure sensor is mounted on the first surface while being adjacent to the first module.

12. The electronic device of claim 11, wherein the biometric sensor is activated if the at least one pressure sensor detects pressure having a specific value or more.

13. The electronic device of claim 1, further comprising:
    a buffer member formed on a surface of the first module, which faces the display.

14. The electronic device of claim 1, further comprising:
    a display driver integrated circuit disposed on one surface of the connecting area to control the display.

15. An electronic device comprising:
    a flexible printed circuit board (FPCB) including a planar area and a bent area;
    a sensor mounted on a first surface of the planar area;
    a display connected with the bent area; and
    a back panel formed on a rear surface of the display,
    wherein the bent area is bent such that the sensor is apart from the display to face the display, and
    wherein an opening is formed in an area of the back panel, which corresponds to a position of the sensor.

16. The electronic device of claim 15, further comprising:
    a display driver integrated circuit disposed on one surface of the planar area to operate the display.

17. A display device comprising:
    a display panel having a plurality of pixels to display content;
    a flexible member including a first area making contact with one surface of the display panel and a second area extending from the one surface of the display panel;
    a display driver integrated circuit disposed in the second area of the flexible member;
    a flexible printed circuit board (FPCB) connected with the second area;
    a back panel formed on a rear surface of the display; and
    a biometric sensor mounted on one surface of the FPCB,
    wherein an opening is formed in an area of the back panel, which corresponds to the biometric sensor.

18. The display device of claim 17, wherein the second area is bent such that the biometric sensor is apart from the display to face the display.

* * * * *